(12) United States Patent
Takahashi et al.

(10) Patent No.: US 7,887,835 B2
(45) Date of Patent: Feb. 15, 2011

(54) COMPOUND COMPRISING A FLUORINE-SUBSTITUTED ALKYL GROUP AND A LIPOSOME CONTRAST MEDIUM COMPRISING THE COMPOUND

(75) Inventors: Kazunobu Takahashi, Kanagawa (JP); Kazuhiro Aikawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 358 days.

(21) Appl. No.: 11/898,968

(22) Filed: Sep. 18, 2007

(65) Prior Publication Data
US 2008/0138285 A1   Jun. 12, 2008

(30) Foreign Application Priority Data

| Sep. 19, 2006 | (JP) | ............................. 2006-252510 |
| Sep. 19, 2006 | (JP) | ............................. 2006-252511 |
| Sep. 20, 2006 | (JP) | ............................. 2006-254062 |
| Sep. 29, 2006 | (JP) | ............................. 2006-267249 |
| Mar. 28, 2007 | (JP) | ............................. 2007-083543 |

(51) Int. Cl.
*A61K 9/127* (2006.01)
(52) U.S. Cl. ...................................... 424/450; 514/759
(58) Field of Classification Search .................. 424/450
See application file for complete search history.

(56) References Cited

FOREIGN PATENT DOCUMENTS

JP   2002193878 A *   7/2002

OTHER PUBLICATIONS

PW Miller, NJ Long, R Vilar, AD Gee. "Synthesis of 11C, 18F, 15O, and 13N Radiolabels for Positron Emission Tomography." Angew. Chem. Int. Ed. 2008, 47, 8998-9033.*

\* cited by examiner

*Primary Examiner*—Frederick Krass
*Assistant Examiner*—Isaac Shomer
(74) *Attorney, Agent, or Firm*—Sughrue Mion, PLLC

(57) ABSTRACT

A steroid ester compound of a terminally-fluorinated alkyl fatty acid, a steroid compound having bis(trifluoromethyl) phenyl group, a phosphatidylserine compound having a terminally-fluorinated alkyl group, a glyceride compound having bis(trifluoromethyl phenyl group, or a glyceride compound having a terminally-fluorinated alkyl group. A vascular lesion can be selectively imaged by using a contrast medium comprising a liposome containing said compound or a salt thereof.

5 Claims, 1 Drawing Sheet
(1 of 1 Drawing Sheet(s) Filed in Color)

COMPOUND COMPRISING A FLUORINE-SUBSTITUTED ALKYL GROUP AND A LIPOSOME CONTRAST MEDIUM COMPRISING THE COMPOUND

CROSS-REFERENCE TO RELATED APPLICATIONS

This application claims benefit of priorities under 35 USC 119 to Japanese Patent Applications No. 2006-252510 filed on Sep. 19, 2006, No. 2006-252511 filed on Sep. 19, 2006, No. 2006-254062 filed on Sep. 20, 2006, No. 2006-267249 filed on Sep. 29, 2006, and No. 2007-083543 filed on Mar. 28, 2007, the disclosures of which are each expressly incorporated by reference herein in their entireties.

FIELD OF THE INVENTION

The present invention relates to a compound comprising a fluorine-substituted alkyl group. More specifically, the present invention relates to a steroid ester compound of a terminally-fluorinated alkyl fatty acid, a steroid compound having bis(trifluoromethyl)phenyl group, a phosphatidylserine compound having a terminally-fluorinated alkyl group, a glyceride compound having bis(trifluoromethyl phenyl group, and a glyceride compound having a terminally-fluorinated alkyl group. The present invention further relates to a liposome which contains said compounds or a salt thereof as a membrane component, and a contrast medium which comprises said liposome.

BACKGROUND ART

A primary example of non-invasive methods for diagnosing arteriosclerosis includes X-ray angiography. This method involves contrasting vascular flows by using a water-soluble iodine-containing contrast medium, and for this reason, the method has a problem of poor distinguishability of pathological tissues from normal tissues. The above method only achieves detection of a lesion where constriction progresses 50% or more, and the method has difficulty in detecting a lesion before onset of attack of an ischemic disease.

As diagnostic methods other than the above, methods of detecting a disease by nuclear magnetic resonance tomography (MRI) have been reported in recent years which use a contrast medium kinetically distributed at a high level in arteriosclerotic plaques. However, any of compounds reported as the contrast medium has a problem when used in diagnostic methods. For example, hematoporphyrin derivatives are reported to have a defect of deposition in the skin and coloring of the skin (see, U.S. Pat. No. 4,577,636 the disclosure of which is expressly incorporated by reference herein in its entirety). As for gadolinium complexes having a perfluorinated side chain which have been reported to accumulate in lipid-rich plaques, accumulation in lipid-rich tissues and organs in vivo, such as fatty livers, renal epitheliums, and tendons of muscular tissues is of concern (see, Circulation, 109, 2890, 2004, the disclosure of which is expressly incorporated by reference herein in its entirety).

From a viewpoint of chemical compounds, a steroid ester of fatty acid wherein all the hydrogen atoms other than those at α-position are substituted with fluorine atoms is known (Tetrahedron, 45, 6467, 1989, the disclosure of which is expressly incorporated by reference herein in its entirety). However, the steroid ester is disclosed in the publication in relation of fluorination by a photoreaction, and its application for a contrast medium is not known.

Alcohol esters having structures of bis(trifluoromethyl) benzoic acid and steroid skeleton are also known. However, these esters have a sterically-hindered structure near the ester group and thus a low degradability in vivo is of concern.

Phosphatidylcholine type compounds with a fluorinated alkyl group (see, for example, Langmuir, 19, 4889, 2003, the disclosure of which is expressly incorporated by reference herein in its entirety) are known. However, phosphatidylserine type compounds are not known.

Further, a compound is known wherein a carboxylic acid having polyaminoethylene residue binds to a diglyceride with a fluorinated alkyl group (see, for example, WO9834910, the disclosure of which is expressly incorporated by reference herein in its entirety). However, a compound having polyamine structure is susceptible to be positively charged. Therefore, generation of toxicity in vivo through interaction with a cell membrane and DNA is of concern.

DISCLOSURE OF THE INVENTION

An object of the present invention is to provide a compound suitable for a lesion-selective liposome contrast medium.

The inventors of the present invention conducted various researches to achieve the aforementioned object. As a result, they found that a steroid ester compound of a terminally-fluorinated alkyl fatty acid, a steroid compound having bis (trifluoromethyl)phenyl group, a fluorinated phosphatidylserine compound, a glyceride compound having bis (trifluoromethyl phenyl group, and a glyceride compound having a terminally-fluorinated alkyl group had superior properties as a component of liposomes as a contrast medium. The present invention was achieved on the basis of these findings.

The present invention thus provides a compound represented by the following general formula (I), or a salt thereof:

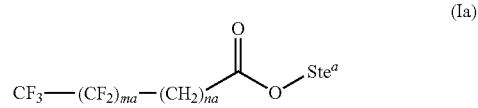
(Ia)

wherein ma represents an integer of 1 to 9; na represents an integer of 2 to 10; $Ste^a$ represents a hydrocarbon group comprising as a partial structure a steroid skeleton represented by the following general formula (II):

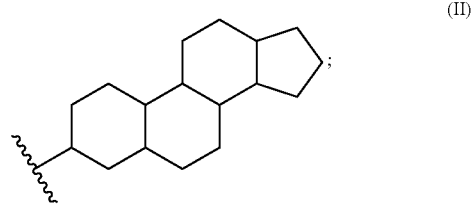
(II)

and one or more of F may be $^{18}F$.

As a preferred embodiment of the present invention, there is provided the aforementioned compound or a salt thereof, wherein Ste$^a$ is a hydrocarbon group represented by the following general formula (III) or (IV).

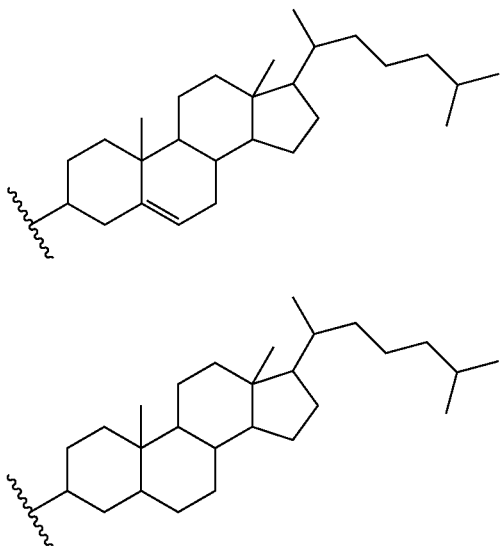

More preferably, the aforementioned compound or a salt thereof, wherein ma is an integer of 3 to 9; na is an integer of 4 to 10 is provided.

The present invention also provides a compound represented by the following general formula (Ib), or a salt thereof:

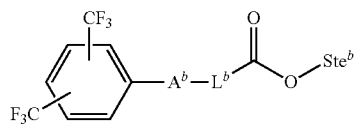

wherein $A^b$ represents oxygen atom or a single bond; $L^b$ represents a divalent bridging group comprising a main chain consisting of 1 to 10 carbon atoms or a single bond provided that $A^b$ and $L^b$ do not represent a single bond at the same time; Ste$^b$ represents a hydrocarbon group comprising as a partial structure a steroid skeleton represented by the above general formula (II). As a preferred embodiment of the present invention, there is provided the aforementioned compound represented by the general formula (Ib) or a salt thereof, wherein Ste$^a$ is a hydrocarbon group represented by the above general formula (III) or (IV). More preferably, the aforementioned compound or a salt thereof, wherein $A^b$ is oxygen atom is provided.

The present invention also provides a compound represented by the following general formula (Ic) or (IIc), or a salt thereof:

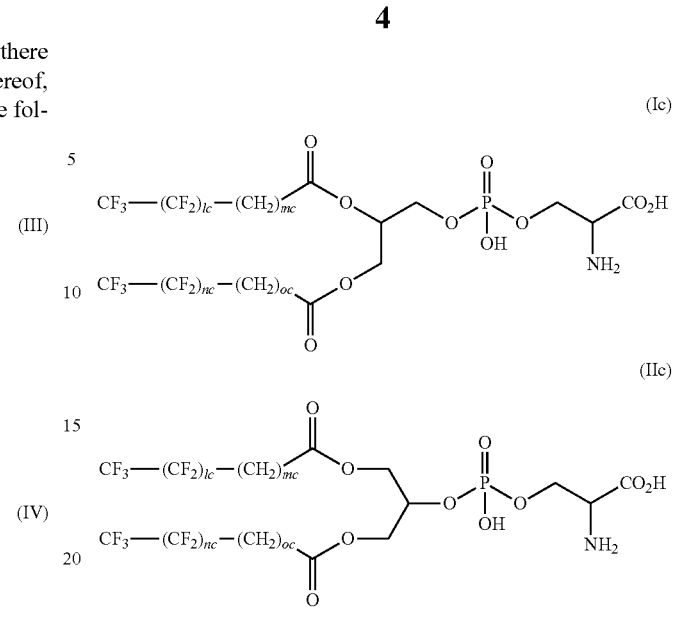

wherein lc and nc each independently represents an integer of 1 to 9; mc and oc each independently represents an integer of 2 to 10; and one or more of F may be $^{18}$F.

As a preferred embodiment of the present invention, there is provided the aforementioned compound represented by the general formula (Ic) or (IIc), or a salt thereof, wherein lc and nc each independently is an integer of 5 to 9; mc and oc each independently is an integer of 5 to 10.

The present invention also provides a compound represented by the following general formula (Id) or (IId), or a salt thereof:

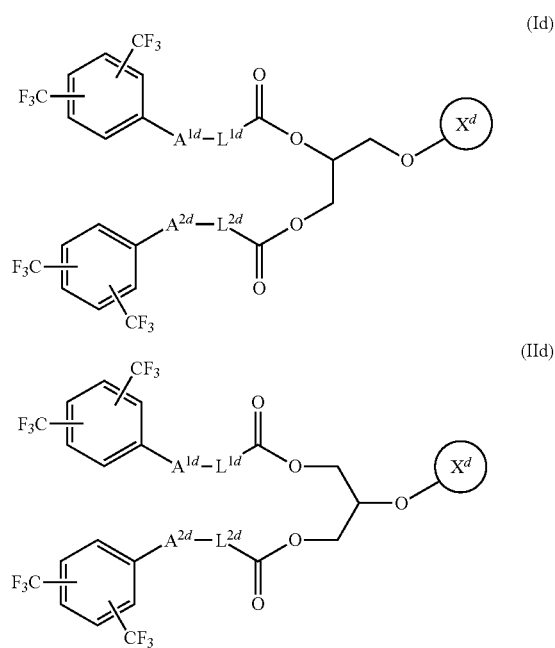

wherein $A^{1d}$ and $A^{1d}$ each independently represents oxygen atom or a single bond; $L^{1d}$ and $L^{2d}$ each independently represents a divalent bridging group comprising a main chain consisting of 5 to 20 carbon atoms; $X^d$ represents a group consisting of 1 to 20 atoms selected from the group consisting of carbon, oxygen, nitrogen, phosphorous, and sulfur atoms, and hydrogen atoms; and one or more of F may be $^{18}$F.

As preferred embodiments of the present invention, there are provided the aforementioned compound represented by the general formula (Id) or (IId), or a salt thereof, wherein $X^d$ is a group represented by the following general formula (IIId):

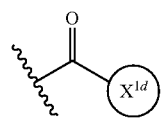

(IIId)

wherein $X^{1d}$ represents a group consisting of 1 to 18 atoms selected from the group consisting of carbon, oxygen, nitrogen, phosphorous and sulfur atoms, and hydrogen atoms; the aforementioned compound represented by the general formula (Id) or (IId), or a salt thereof, wherein $X^d$ is a group represented by the following general formula (IVd):

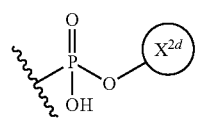

(IVd)

wherein $X^{2d}$ represents a group consisting of 1 to 16 atoms selected from the group consisting of carbon, oxygen, nitrogen, phosphorous, and sulfur atoms, and hydrogen atoms; the aforementioned compound represented by the general formula (Id) or (IId), or a salt thereof, wherein $X^d$ is a group consisting of 1 to 15 atoms selected from the group consisting of carbon, oxygen, nitrogen, phosphorous, and sulfur atoms, and hydrogen atoms; and the aforementioned compound represented by the general formula (Id) or (IId), or a salt thereof, wherein $X^d$ is a group consisting of 1 to 15 atoms selected from the group consisting of carbon, oxygen, nitrogen, and phosphorous atoms, and hydrogen atoms. More preferably, the aforementioned compound or a salt thereof, wherein $A^{1d}$ and $A^{2d}$ each is oxygen atom; and the aforementioned compound or a salt thereof wherein $L^{1d}$ and $L^{2d}$ each independently is a divalent bridging group comprising a main chain consisting of 10 to 20 carbon atoms are provided.

The present invention also provides a compound represented by the following general formula (Ie) or (IIe), or a salt thereof:

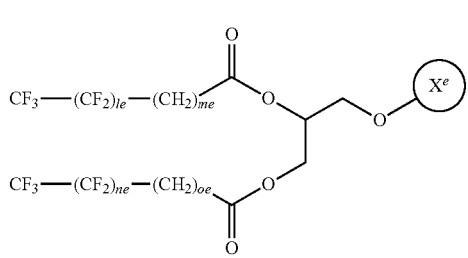

(Ie)

-continued

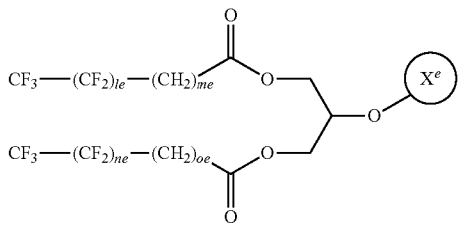

(IIe)

wherein le and ne each independently represents an integer of 1 to 10; me and oe each independently represents an integer of 2 to 10; $X^e$ represents a group consisting of atoms selected from the group consisting of carbon, oxygen, nitrogen, sulfur, and hydrogen atoms, provided that, in $X^e$, total number of carbon, oxygen, nitrogen, and sulfur atoms is 3 to 40, number of carbon atom is 1 to 38, total number of oxygen, nitrogen, and sulfur atoms is 2 to 13, number of nitrogen atom is 0 to 3, and number of sulfur atom is 0 to 3; one or more of F may be $^{18}$F.

As preferred embodiments of the present invention, there are provided the aforementioned compound represented by the general formula (Ie) or (IIe), wherein $X^e$ is a group represented by the following general formula (IIIe):

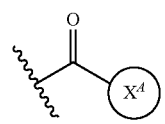

(IIIe)

wherein $X^A$ represents a group consisting of atoms selected from the group consisting of carbon, oxygen, nitrogen, sulfur, and hydrogen atoms, provided that, in $X^A$, total number of carbon, oxygen, nitrogen, and sulfur atoms is 1 to 38, number of carbon atom is 0 to 37, total number of oxygen, nitrogen, and sulfur atoms is 1 to 12, number of nitrogen atom is 0 to 3, and number of sulfur atom is 0 to 3. More preferably, the aforementioned compound or a salt thereof, wherein the group of atoms constituting $X^A$ contains no sulfur atom; the aforementioned compound or a salt thereof, wherein the total number of carbon, oxygen, nitrogen, and sulfur atoms is 1 to 28; and the aforementioned compound or a salt thereof, wherein the total number of carbon, oxygen, nitrogen, and sulfur atoms is 1 to 18, are provided.

As other preferred embodiments of the present invention, there are provided the aforementioned compound represented by the general formula (Ie) or (IIe), wherein $X^e$ is a group represented by the following general formula (IVe):

(IVe)

wherein $X^B$ represents a group consisting of atoms selected from the group consisting of carbon, oxygen, nitrogen, sulfur, and hydrogen atoms, provided that, in $X^B$, total number of carbon, oxygen, nitrogen, and sulfur atoms is 2 to 39, number of carbon atom is 0 to 37, total number of oxygen, nitrogen, and sulfur atoms is 2 to 13, number of nitrogen atom is 0 to 3, and number of sulfur atom is 0 to 3. More preferably, the aforementioned compound or a salt thereof, wherein the group of atoms constituting $X^B$ contains no sulfur atom; the aforementioned compound or a salt thereof, wherein the total number of carbon, oxygen, nitrogen, and sulfur atoms is 2 to 29; and the aforementioned compound or a salt thereof, wherein the total number of carbon, oxygen, nitrogen, and sulfur atoms is 2 to 19 are provided.

As still another preferred embodiments of the present invention, there is provided any of the aforementioned compounds wherein at least one of F is $^{18}F$ (radioisotope).

From another aspect of the present invention, a liposome containing as a membrane component any of the aforementioned compounds or a salt thereof is provided by the present invention, and according to a preferred embodiment thereof, the liposome containing a phosphatidylcholine and a phosphatidylserine as membrane components is provided.

From a still further aspect of the present invention, there is provided a contrast medium comprising the aforementioned liposome. According to preferred embodiments of the above invention, there are provided the aforementioned contrast medium, which is used for imaging a vascular disease; the aforementioned contrast medium, which is used for imaging of vascular smooth muscle cells abnormally proliferating under influence of foam macrophages; the aforementioned contrast medium, which is used for imaging of a tissue or lesion in which macrophages localize; the aforementioned contrast medium, wherein the tissue in which macrophages localize is selected from the group consisting of tissues of liver, spleen, air vesicle, lymph node, lymph vessel, and renal epithelium; and the aforementioned contrast medium, wherein the lesion in which macrophages localize is selected from the group consisting of lesions of tumor, inflammation, and infection.

Furthermore, the present invention provides use of the aforementioned compound or a salt thereof for the manufacture of a contrast medium; use of the aforementioned liposome for the manufacture of a contrast medium; a method of contrast imaging, which comprises administering liposomes containing the aforementioned compound as a membrane component to a mammal including human; and a method of contrast imaging of a lesion of a vascular disease, which comprises administering liposomes containing the aforementioned compound as a membrane component to a mammal including human.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

Figure 1:
FIG. 1 is a photograph presenting the result of MRI imaging (proton MRI, T1-enhanced) of arteriosclerotic lesion in aortic arch of WHHL rabbit by using a liposome of the present invention.

When a functional group is referred to as "which may be substituted" or "which may have a substituent" in the specification, it is meant that the functional group may have one or more substituents. Unless otherwise specifically mentioned, number, substituting position, and type of a substituent to be bound are not particularly limited. When a functional group has two or more substituents, they may be the same or different. In the specification, when a functional group has a substituent, examples of the substituent include a halogen atom (the "halogen atom" in the specification include any of fluorine, chlorine, bromine, and iodine), an alkyl group (the "alkyl group" in the specification include straight, branched, cyclic alkyl groups, and an alkyl group consisting of a combination thereof, and the cyclic alkyl group include a polycyclic alkyl group such as a bicycloalkyl group. Alkyl moieties of substituents containing the alkyl moieties have the same meaning.), an alkenyl group (including a cycloalkenyl group and a bicycloalkenyl group), an alkynyl group, an aryl group, a heterocyclic group, cyano group, hydroxyl group, nitro group, carboxyl group, an alkoxyl group, an aryloxy group, a silyloxy group, a heterocyclyoxy group, an acyloxy group, carbamoyloxy group, an alkoxycarbonyloxy group, an aryloxycarbonyloxy group, amino group (including anilino group), an acylamino group, aminocarbonylamino group, an alkoxycarbonylamino group, an aryloxycarbonylamino group, sulfamoylamino group, an alkyl- or arylsulfonylamino group, mercapto group, an alkylthio group, an arylthio group, a heterocyclylthio group, sulfamoyl group, sulfo group, an alkyl- or arylsulfinyl group, an alkyl- or arylsulfonyl group, an acyl group, an aryloxycarbonyl group, an alkoxycarbonyl group, carbamoyl group, an aryl- or heterocyclylazo group, imido group, phosphino group, phosphinyl group, phosphinyloxy group, phosphinylamino group, and silyl group.

In the general formula (Ia), ma represents an arbitrary integer of 1 to 9, and na represents an arbitrary integer of 2 to 10. More preferably, ma represents an arbitrary integer of 3 to 9 and na represents an optional integer of 4 to 10.

Each of $Ste^a$ in the general formula (Ia) and $Ste^b$ in the general formula (Ib) represents a hydrocarbon group comprising as a partial structure a steroid skeleton represented by the general formula (II). $Ste^a$ and $Ste^b$ are constituted by addition of arbitrary substituents to the skeleton, and number, substituting position, and type of the substituent are not particularly limited. The number of the substituents is generally 30 or less, more preferably 15 or less, most preferably 10 or less. Preferable examples of the substituent include an alkyl group, an alkenyl group, an alkynyl group, hydroxyl group, carboxyl group, an alkoxyl group, an acyloxy group, amino group, an acylamino group, an acyl group, an alkoxycarbonyl group, and oxo group. The more preferable examples include an alkyl group, hydroxyl group, carboxyl group, an acyloxy group, an acyl group, and oxo group. $Ste^a$ or $Ste^b$ may include an unsaturated bond in the structure. Type, position, and number of the unsaturated bond are not particularly limited. However, the number is generally 5 or less, and preferably 3 or less.

As $Ste^a$ or $Ste^b$, preferable examples include a hydrocarbon group represented by the following general formula (III) or (IV) derived form cholesterol or cholestanol.

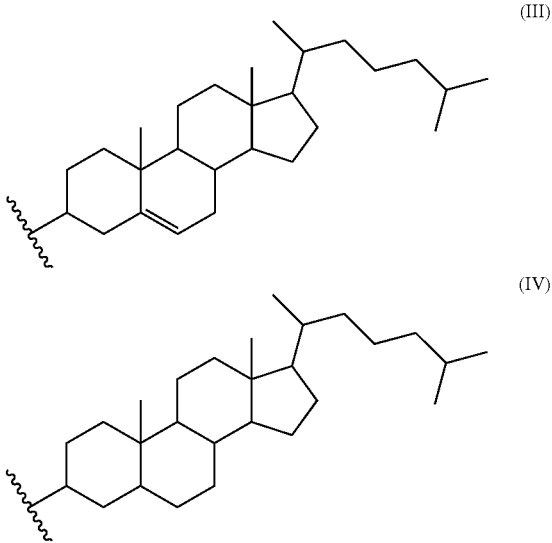

(III)

(IV)

The group represented by the above general formula (III) or (IV), may have an arbitrary number and type of substituent at any position, however, preferably has no substituents. Steric configuration of each asymmetric carbon in the group represented by the general formula (III) or (IV) may independently be either R-configuration or S-configuration, or the group may be present as a mixture thereof.

In the general formula (Ib), $L^b$ represents a divalent bridging group comprising a main chain consisting of 1 to 10 carbon atoms or a single bond. However, when $L_b$ represents a single bond, $A^b$ represents oxygen atom. The main chain in $L_b$ represents a group of atoms in the atoms constituting $L_b$, which binds $A^b$ and —CO— adjacent to $L^b$ with minimum number of atoms. The number of carbon atoms constituting the main chain of $L^b$ is more preferably 1 to 5. Atoms other than carbon atom, which constitute $L^b$ are not particularly limited. However, hydrogen atom, oxygen atom, nitrogen atom, and sulfur atom are preferred and hydrogen atom and oxygen atom are more preferred. Number of the atoms other than carbon atoms and hydrogen atoms which constitute $L^b$ is also not particularly limited, and generally 10 or less, preferably 5 or less, most preferably 3 or less. $L^b$ may be straight, branched, cyclic, or a combination thereof, preferably straight or branched, most preferably straight. $L^b$ may be saturated or include an unsaturated bond. Type, position and number of the unsaturated bond are not particularly limited. Preferable examples of the bridging group represented by $L^b$ include an alkylene group having 1 to 10 carbons and an alkenylene group having 1 to 10 carbons.

In the general formula (Ic) or (IIc), lc and nc each independently represents an arbitrary integer of 1 to 9, more preferably an arbitrary integer of 3 to 9, and most preferably an arbitrary integer of 5 to 9. Each of mc and oc independently represents an arbitrary integer of 2 to 10, more preferably an arbitrary integer of 4 to 10, and most preferably an optional integer of 5 to 9.

In the general formula (Id) or (IId), $L^{1d}$ and $L^{2d}$ each independently represents a divalent bridging group comprising a main chain consisting of 5 to 20 carbon atoms. The main chain in $L^{1d}$ represents a group of atoms in the atoms constituting $L^{1d}$, which binds $A^{1d}$ and —CO— adjacent to $L^{1d}$ with minimum number of atoms. The main chain in $L^{2d}$ represents a group of atoms in the atoms constituting $L^{2d}$, which binds $A^{2d}$ and —CO— adjacent to $L^{2d}$ with minimum number of atoms. Each of the main chains preferably consists of 10 to 20 carbon atoms, most preferably consists of 14 to 18 carbon atoms. The bridging group may consist of the above main chain with only hydrogen atoms bound thereto, or may have substituents other than hydrogen atoms. The substituent preferably consists of atoms selected form a group consisting of carbon atom, hydrogen atom, oxygen atom, nitrogen atom, and sulfur atom, and more preferably consists of atoms selected form a group consisting of carbon atom, hydrogen atom, and oxygen atom. $L^{1d}$ and $L^{2d}$ each independently is preferred to have no such substituents. $L^{1d}$ and $L^{2d}$ each independently may be straight, branched, cyclic, or a combination thereof, preferably straight or branched, and most preferably straight. $L^{1d}$ and $L^{2d}$ each may be saturated or include an unsaturated bond. Type, position and number of the unsaturated bond are not particularly limited. Particularly preferable examples of $L^{1d}$ or $L^{2d}$ include a straight alkylene group having 5 to 20 carbons. Further, $L^{1d}$ and $L^{2d}$ may be the same or different, and $L^{1d}$ and $L^{2d}$ is preferably the same.

$X^d$ represents a group consisting of 1 to 20 atoms selected from the group consisting of carbon, oxygen, nitrogen, phosphorous, and sulfur atoms, and hydrogen atoms. Between the compounds represented by the general formula (Id) or (IId) having a group of such bulkiness as $X^d$, suitability for forming liposome and the properties of the liposome as a contrast medium are almost the same. As the group represented by $X^d$, examples include the substituents exemplified above for a substituent, or a combination thereof, provided that silyl group or the like is excluded, and a hydrophilic group or a group having affinity to a polar solvent such as water is preferred. Number of the atoms selected from the group consisting of carbon, oxygen, nitrogen, phosphorous, and sulfur atoms is preferably 15 or less, more preferably 5 to 15. $X^d$ is more preferably a group consisting of 1 to 20, preferably 1 to 15 atoms selected from the group consisting of carbon, oxygen, nitrogen, and phosphorous atoms, and hydrogen atoms.

As a preferable group as $X^d$, examples include a group having carbonyl group at the site directly binding to glycerol, and a group having phosphate group at the site directly binding to glycerol.

As types of the group represented by $X^{1d}$ in the aforementioned formula (IIId) or $X^{2d}$ in the aforementioned formula (IVd), examples include the same groups as the groups exemplified for $X^d$. More preferable examples include an alkyl group, an alkenyl group, an alkynyl group, an aryl group, a heterocyclic group, hydroxyl group, carboxyl group, an alkoxyl group, an aryloxy group, a heterocycloxy group, an acyloxy group, carbamoyloxy group, an alkoxycarbonyloxy group, an aryloxycarbonyloxy group, amino group (including anilino group and quaternary ammonium group), an acylamino group, aminocarbonylamino group, an alkoxycarbonylamino group, an aryloxycarbonylamino group, an acyl group, an aryloxycarbonyl group, an alkoxycarbonyl group, carbamoyl group, and a combination thereof, although the examples of the group represented by $X^{1d}$ or $X^{2d}$ are not particularly limited to the above examples.

Bis(trifluoromethyl)phenyl group in the compound represented by the above general formula (Ib), (Id), or (IId) may have a substituent, however, preferably have no substituents. The substitution positions of the two trifluoromethyl groups are not particularly limited, and each trifluoromethyl group is more preferably in meta-position to $-A^{b-}$, $-A^{1d-}$, or $-A^{2d-}$.

In the general formula (Ie) or (IIe), le and ne each independently represents an integer of 1 to 10. Each of le and ne independently is preferably an integer of 3 to 10, more preferably an integer of 5 to 10. Each of me and oe independently represents an integer of 2 to 10. Each of me and oe independently is preferably an integer of 2 to 8, more preferably an integer of 2 to 6.

$X^e$ represents a group consisting of atoms selected from the group consisting of carbon, oxygen, nitrogen, sulfur, and hydrogen atoms, and total number of carbon, oxygen, nitrogen, and sulfur atoms which constitute $X^e$ is 3 to 40. Between the compounds represented by the general formula (Ie) or (IIe) having a group of such bulkiness as $X^e$, suitability for forming liposome and the properties of the liposome as a contrast medium are almost the same.

The monovalent group represented by $X^e$ may be straight, branched, cyclic, or a combination thereof. In the group of atoms constituting $X^e$, "total number of hetero atoms (oxygen atom, nitrogen atom, and sulfur atom)/total number of carbon atoms" is preferably 0.4 or more, more preferably 0.4 or more and 1.0 or less, and most preferably 0.5 or more and 1.0 or less.

The monovalent group represented by $X^e$ preferably has no sulfur atom, i.e., the hetero atoms in $X^e$ preferably consists of only oxygen atom and nitrogen atom. Further, number of nitrogen atoms in $X^e$ is 0 to 3, preferably 0 to 2, more preferably 0 to 1.

Further, $X^e$ preferably has at least any one of the structures of morpholine, oligo ethylene glycol, and polyol. The position, number, repeating unit, and repeating number are not particularly limited.

$X^e$ is also preferably a group represented by the following general formula (IIIe):

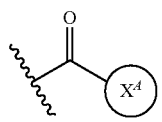

(IIIe)

wherein $X^A$ represents a group consisting of atoms selected from the group consisting of carbon, oxygen, nitrogen, sulfur, and hydrogen atoms, provided that, total number of carbon, oxygen, nitrogen, and sulfur atoms which constitute $X^A$ is 1 to 38, wherein number of carbon atom is 0 to 37, total number of oxygen, nitrogen, and sulfur atoms is 1 to 12, number of nitrogen atom is 0 to 3, and number of sulfur atom is 0 to 3.

The monovalent group represented by $X^A$ may be straight, branched, cyclic, or a combination thereof. In the group of atoms constituting $X^A$, "(total number of hetero atoms+1)/ (total number of carbon atoms+1)" is preferably 0.4 or more, more preferably 0.4 or more and 1.0 or less, and most preferably 0.5 or more and 1.0 or less. Further, number of nitrogen atoms in $X^A$ is generally 0 to 3, preferably 0 to 2, more preferably 0 to 1.

Further, $X^A$ preferably has at least any one of the structures of morpholine, oligo ethylene glycol, and polyol. The position, number, repeating unit, and repeating number are not particularly limited.

$X^e$ is also preferably a group represented by the following general formula (IVe):

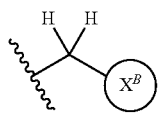

(IVe)

wherein $X^B$ represents a group consisting of atoms selected from the group consisting of carbon, oxygen, nitrogen, sulfur, and hydrogen atoms, provided that total number of carbon, oxygen, nitrogen, and sulfur atoms which constitute $X^B$ is 2 to 39, wherein number of carbon atom is 0 to 37, total number of oxygen, nitrogen, and sulfur atoms is 2 to 13, number of nitrogen atom is 0 to 3, and number of sulfur atom is 0 to 3.

The monovalent group represented by $X^B$ may be straight, branched, cyclic, or a combination thereof. In the group of atoms constituting $X^B$, "(total number of hetero atoms+1)/ (total number of carbon atoms+1)" is preferably 0.4 or more, more preferably 0.4 or more and 1.0 or less, and most preferably 0.5 or more and 1.0 or less. Further, number of nitrogen atoms in $X^B$ is generally 0 to 3, preferably 0 to 2, more preferably 0 to 1.

Further, $X^B$ preferably has at least any one of the structures of morpholine, oligo ethylene glycol, and polyol. The position, number, repeating unit, and repeating number are not particularly limited.

The compounds of the present invention may have one or more asymmetric centers. In such compounds, stereoisomers such as optically active substances and diastereomers based on the asymmetric centers may exist. Any of arbitrary stereoisomers in pure forms, arbitrary mixtures of stereoisomers, racemates and the like fall within the scope of the present invention. Further, the compounds of the present invention may have one or more olefinic double bonds. The configuration thereof may be either E-configuration or Z-configuration, or the compounds may be present as a mixture thereof. The compounds of the present invention may also exist as tautomers. Any tautomers or mixtures thereof fall within the scope of the present invention. Further, the compounds of the present invention may form a salt, and the compounds in a free form or the compounds in the form of a salt may form a hydrate or a solvate. All of these substances also fall within the scope of the present invention. The type of the salt is not particularly limited, and the salt may be an acid addition salt, or a base addition salt.

Preferred examples of the compounds of the present invention will be shown below. However, the compounds of the present invention are not limited to these examples.

Preferred examples of the compounds represented by the general formula (Ia) will be shown below.

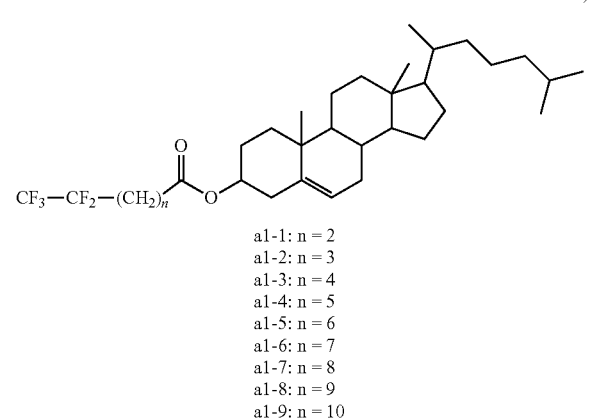

a1)

a1-1: n = 2
a1-2: n = 3
a1-3: n = 4
a1-4: n = 5
a1-5: n = 6
a1-6: n = 7
a1-7: n = 8
a1-8: n = 9
a1-9: n = 10

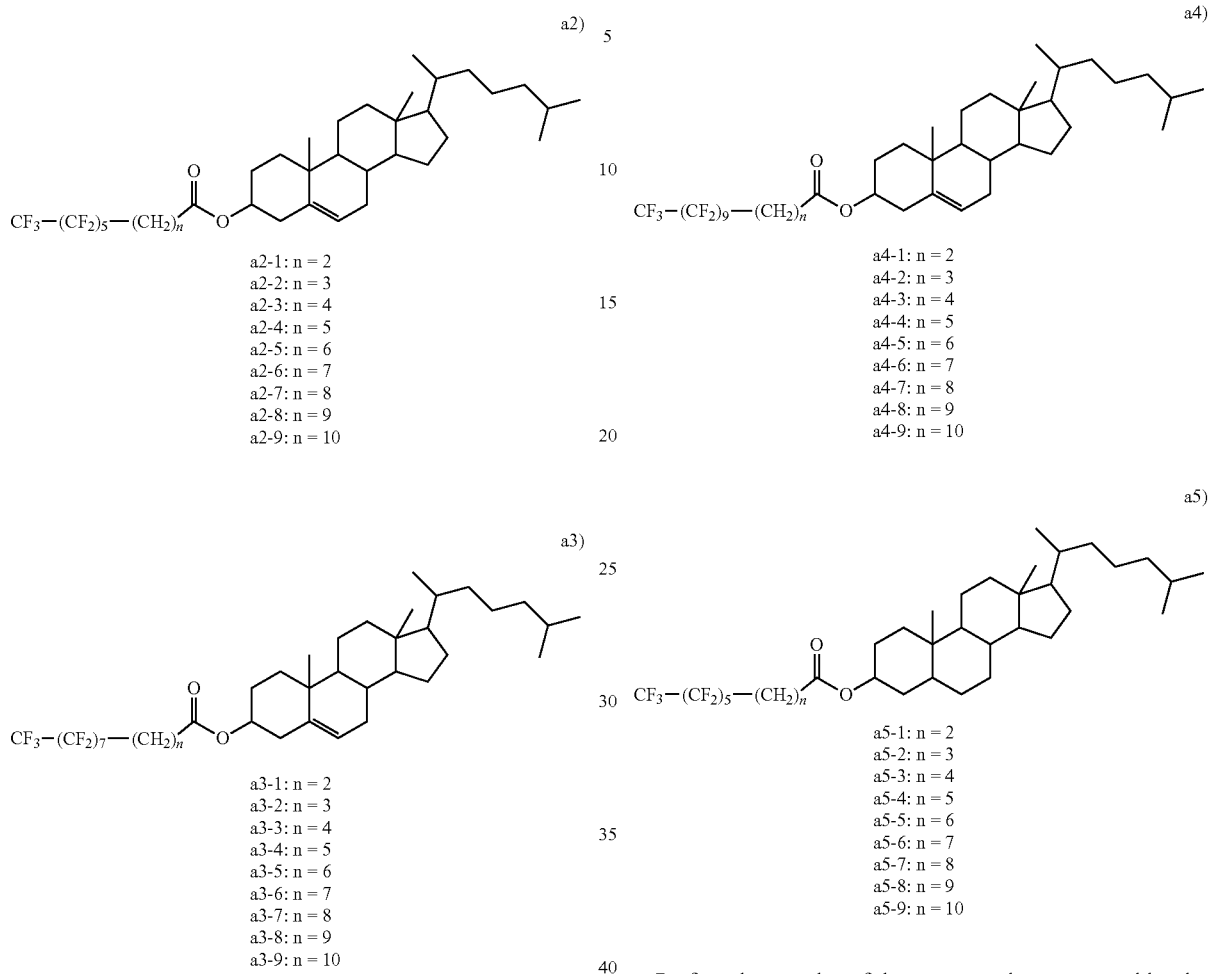
Preferred examples of the compounds represented by the general formula (Ib) will be shown below.
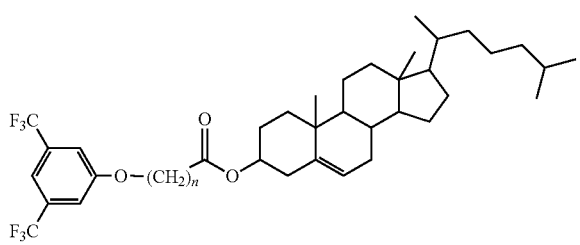
b1-1: n = 0
b1-2: n = 1
b1-3: n = 2
b1-4: n = 3
b1-5: n = 4
b1-6: n = 5
b1-7: n = 7
b1-8: n = 10
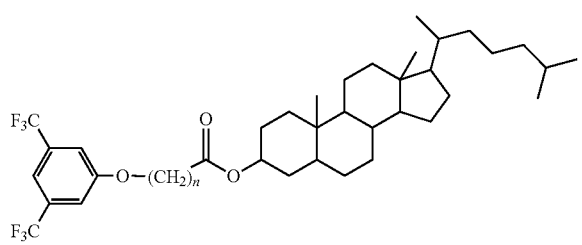
b2-1: n = 0
b2-2: n = 1
b2-3: n = 2
b2-4: n = 3
b2-5: n = 4
b2-6: n = 5
b2-7: n = 7
b2-8: n = 10

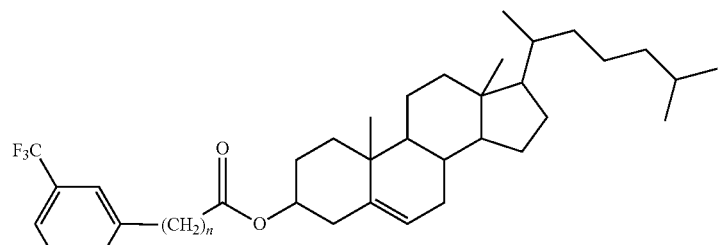
b3)
b3-1: n = 1
b3-2: n = 2
b3-3: n = 3
b3-4: n = 4
b3-5: n = 5
b3-6: n = 7
b3-7: n = 8
b3-8: n = 10
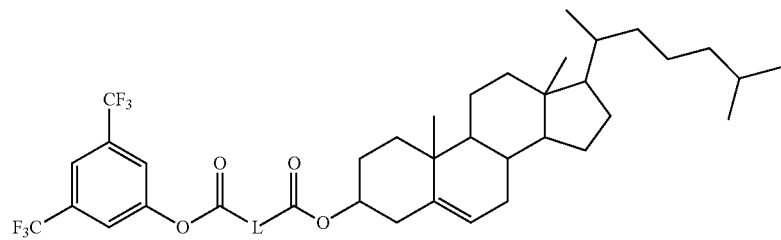
b4)
b4-1: L = —CH$_2$—
b4-2: L = —(CH$_2$)$_2$—
b4-3: L = —CH=CH—
b4-4: L = —(CH$_2$)$_3$—
b4-5: L = —(CH$_2$)$_5$—
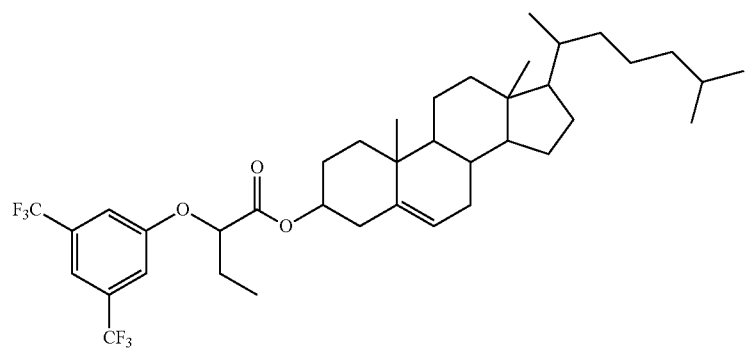
b5)

Preferred examples of the compounds represented by the general formula (Ic) and (IIc) will be shown below.

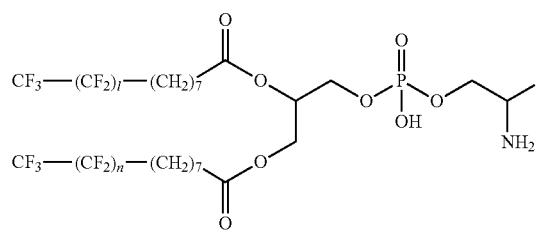

c1)

c1-1: l = n = 1
c1-2: l = n = 2
c1-3: l = n = 3
c1-4: l = n = 4
c1-5: l = n = 5
c1-6: l = n = 6
c1-7: l = n = 7
c1-8: l = n = 8
c1-9: l = n = 9
c1-10: l = 5, n = 7

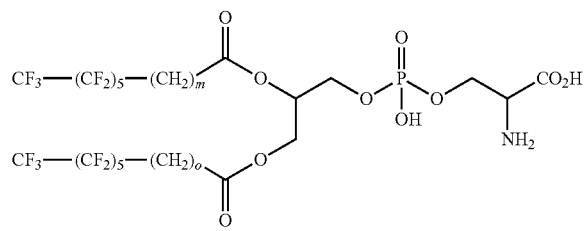

c2)

c2-1: m = o = 2
c2-2: m = o = 3
c2-3: m = o = 4
c2-4: m = o = 5
c2-5: m = o = 6
c2-6: m = o = 8
c2-7: m = o = 9
c2-8: m = o = 10
c2-9: m = 7, o = 9

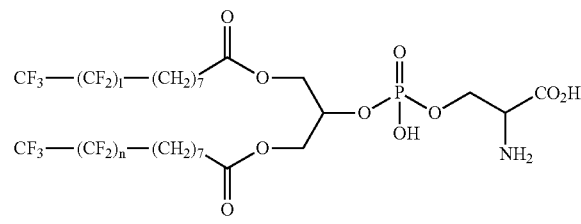

c3)

c3-1: l = n = 1
c3-2: l = n = 2
c3-3: l = n = 3
c3-4: l = n = 4
c3-5: l = n = 5
c3-6: l = n = 6
c3-7: l = n = 7
c3-8: l = n = 8
c3-9: l = n = 9
c3-10: l = 5, n = 7

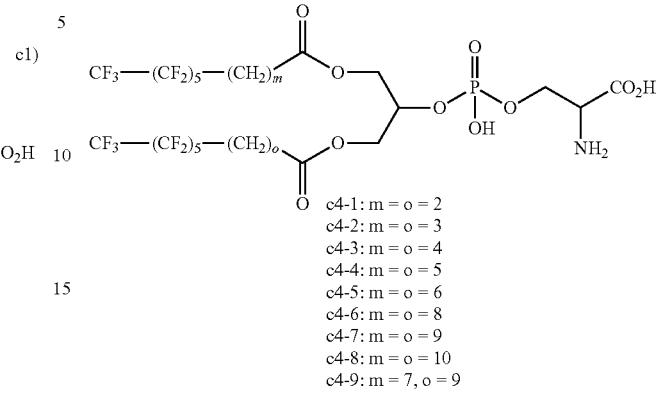

c4)

c4-1: m = o = 2
c4-2: m = o = 3
c4-3: m = o = 4
c4-4: m = o = 5
c4-5: m = o = 6
c4-6: m = o = 8
c4-7: m = o = 9
c4-8: m = o = 10
c4-9: m = 7, o = 9

Preferred examples of the compounds represented by the general formula (Id) and (IId) will be shown below.

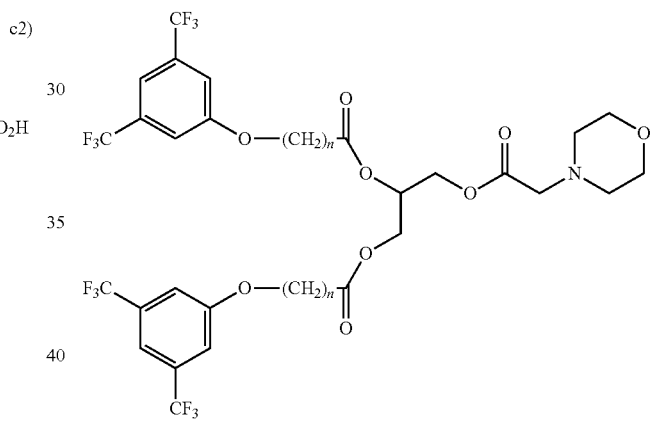

d1)

d1-1: n = 5    d1-6: n = 10
d1-2: n = 6    d1-7: n = 12
d1-3: n = 7    d1-8: n = 15
d1-4: n = 8    d1-9: n = 18
d1-5: n = 9    d1-10: n = 20

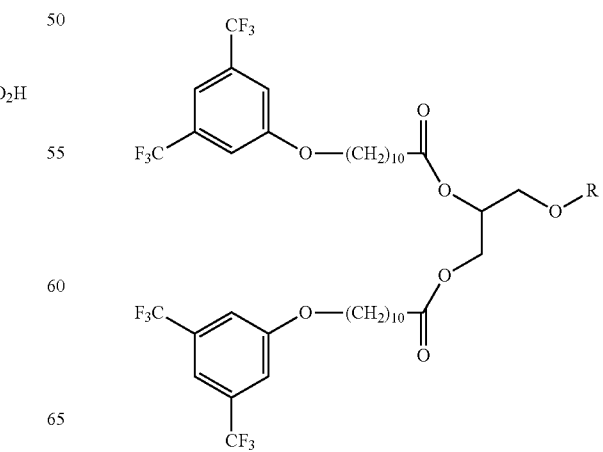

d2)

-continued
R =
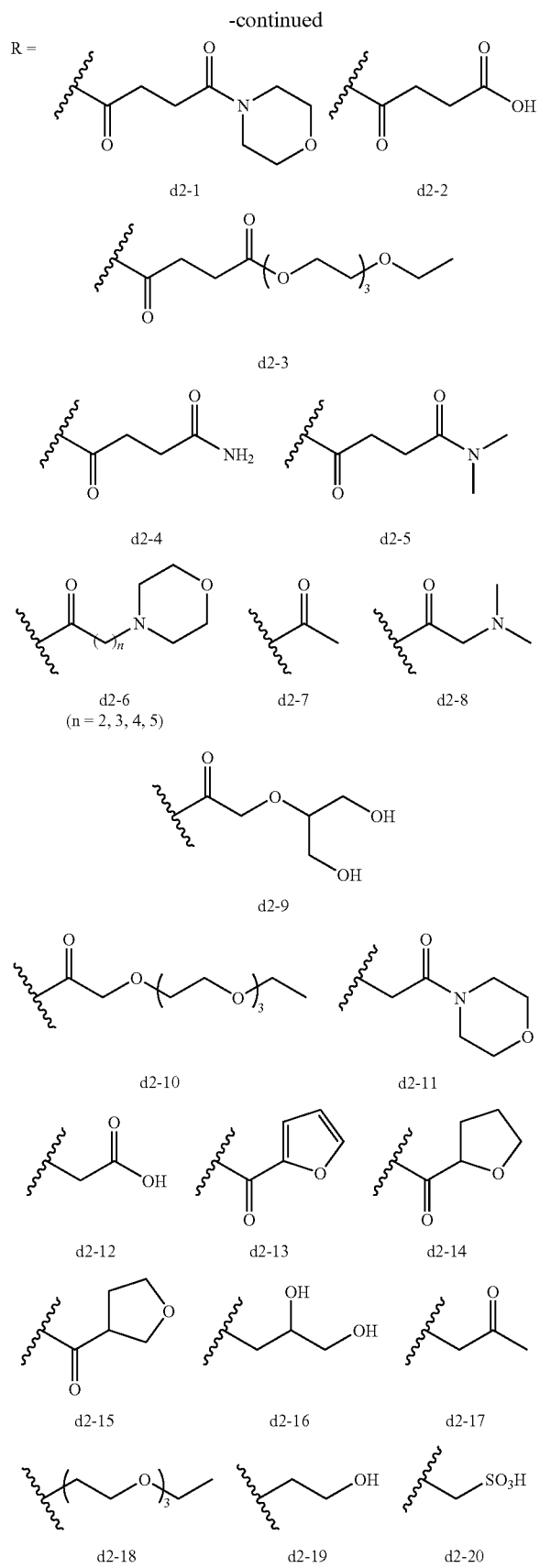
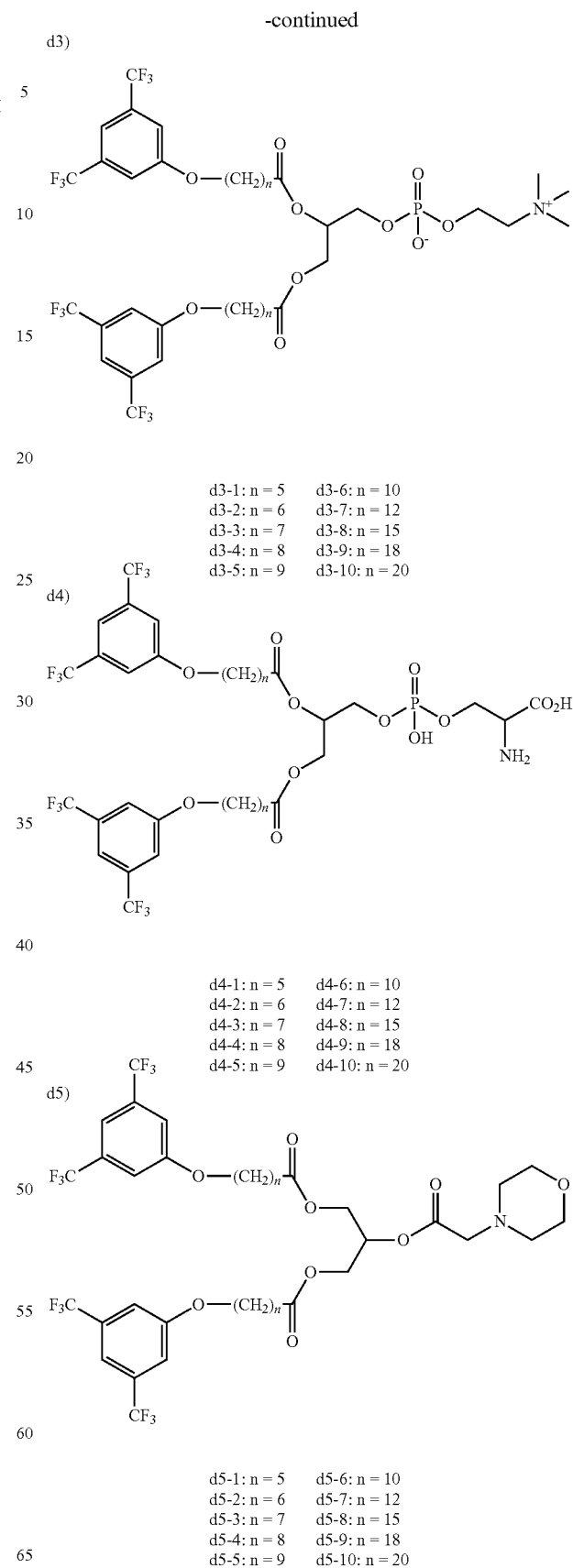
d3-1: n = 5   d3-6: n = 10
d3-2: n = 6   d3-7: n = 12
d3-3: n = 7   d3-8: n = 15
d3-4: n = 8   d3-9: n = 18
d3-5: n = 9   d3-10: n = 20
d4-1: n = 5   d4-6: n = 10
d4-2: n = 6   d4-7: n = 12
d4-3: n = 7   d4-8: n = 15
d4-4: n = 8   d4-9: n = 18
d4-5: n = 9   d4-10: n = 20
d5-1: n = 5   d5-6: n = 10
d5-2: n = 6   d5-7: n = 12
d5-3: n = 7   d5-8: n = 15
d5-4: n = 8   d5-9: n = 18
d5-5: n = 9   d5-10: n = 20

-continued
d6)
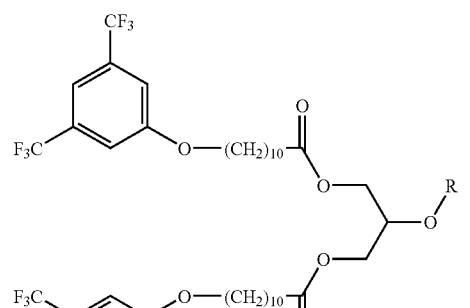
d6-1     d6-2
d6-3     d6-4
d6-5
Preferred examples of the compounds represented by the general formula (Ie) and (IIe) will be shown below.
e1)
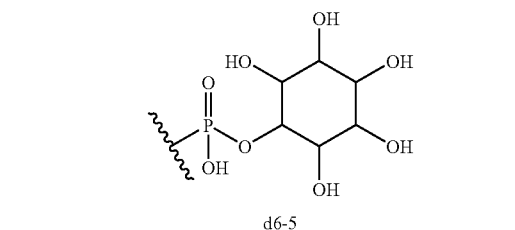
e1-1: l = n = 1; m = o = 7
e1-2: l = n = 3; m = o = 7
e1-3: l = n = 5; m = o = 2
e1-4: l = n = 5; m = o = 4
e1-5: l = n = 5; m = o = 6
e1-6: l = n = 5; m = o = 7
e1-7: l = n = 5; m = o = 8
e1-8: l = n = 5; m = o = 10
e1-9: l = n = 7; m = o = 7
e1-10: l = n = 10; m = o = 7
-continued
e2)
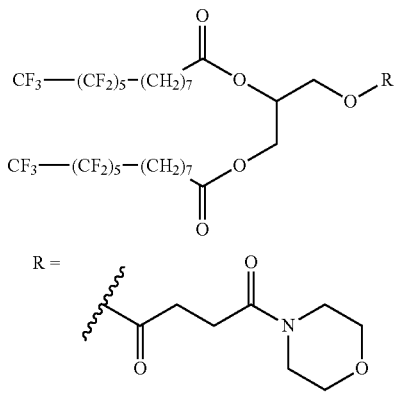
R =
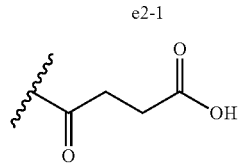
e2-1
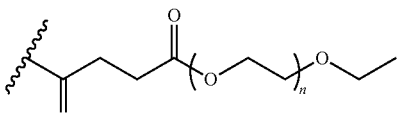
e2-2
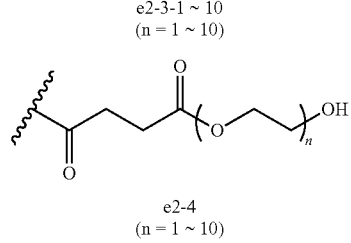
e2-3-1 ~ 10
(n = 1 ~ 10)
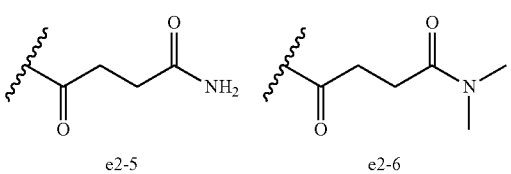
e2-4
(n = 1 ~ 10)
e2-5     e2-6
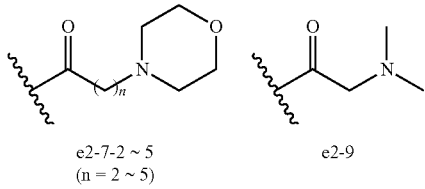
e2-7-2 ~ 5       e2-9
(n = 2 ~ 5)
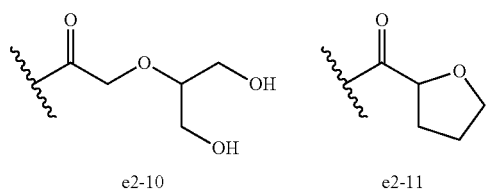
e2-10     e2-11

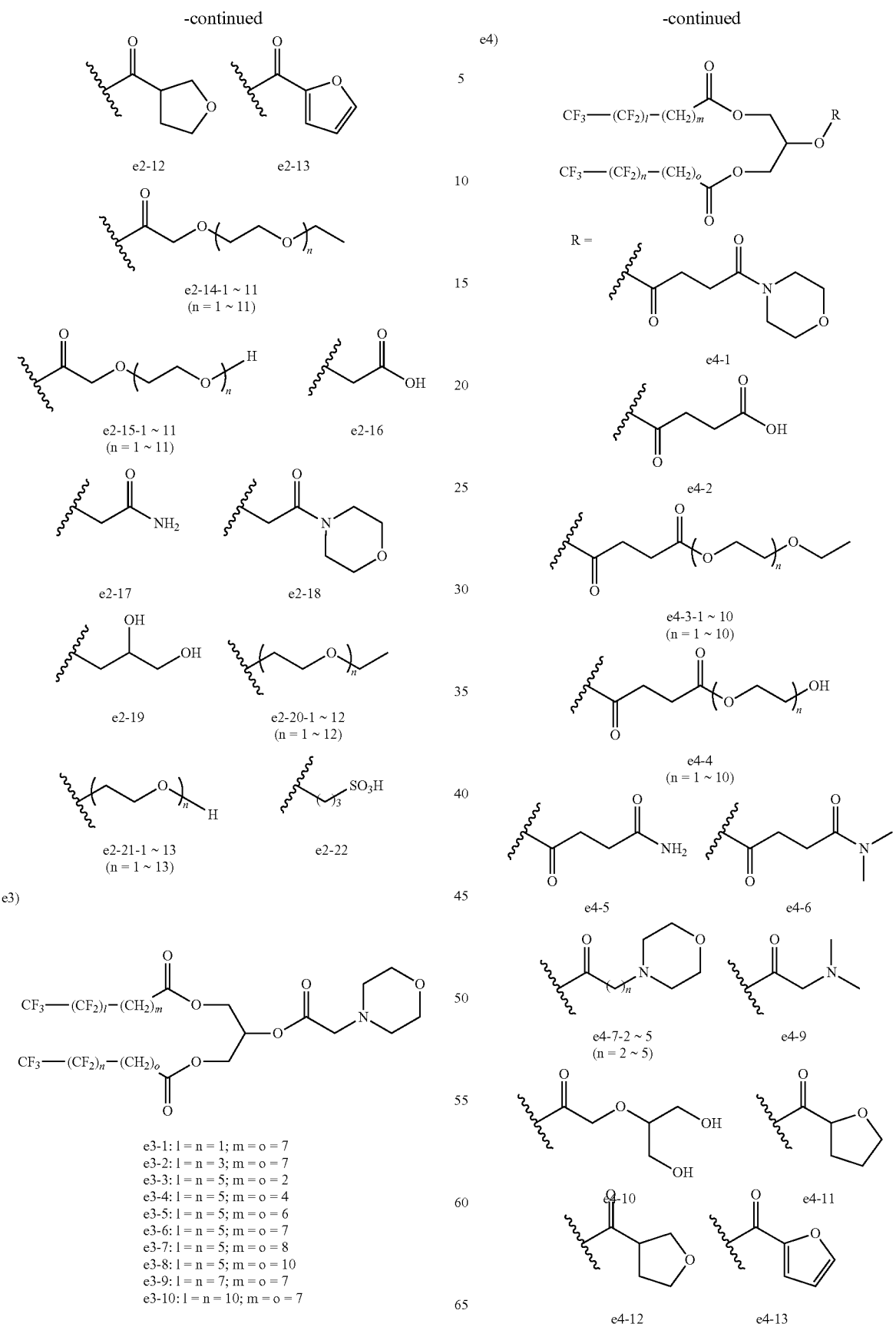

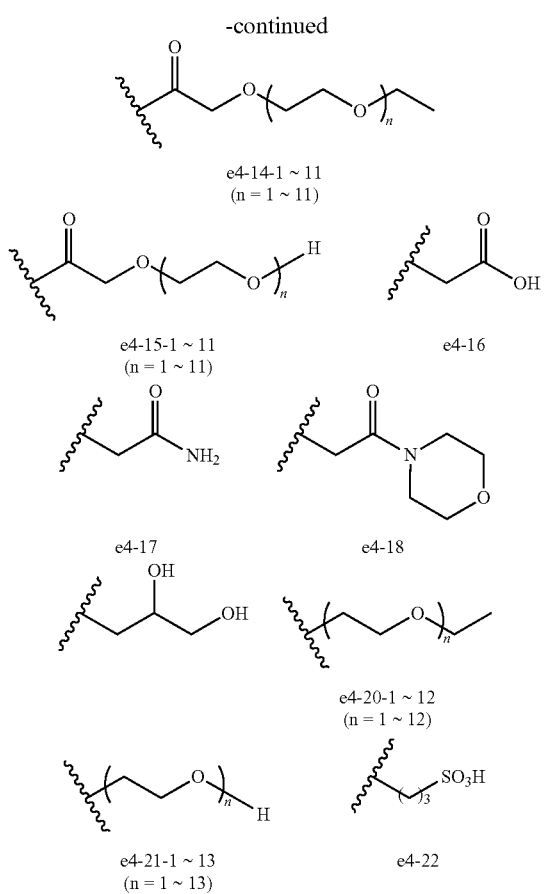

In each of the general formulae (Ia), (Ib), (Ic), (IIc), (Id), (IId), (Ie), and (IIe), one or more of fluorine atoms (F) included in each structure may be $^{18}$F.

As the compound represented by each of the general formulae (Ia), (Ic), (IIc), (Ie), and (IIe) wherein at least one of the fluorine atoms is $^{18}$F, a compound having 1 or more and 10 or less $^{18}$F is preferred, a compound having 1 or more and 5 or less $^{18}$F is more preferred, and a compound having 1 or more and 3 or less $^{18}$F is most preferred, for the compound represented by any of the above general formulae. Although the substitution position of $^{18}$F is not particularly limited, the position is preferred to be CF$_3$ terminal of the fluorinated fatty acid.

As the compound represented by each of the general formulae (Ib), (Id), and (IId) wherein at least one of the fluorine atoms in the compound is $^{18}$F, a compound having 1 or more and 6 or less $^{18}$F is preferred, a compound having 1 or more and 3 or less $^{18}$F is more preferred, for the compound represented by any of the above general formulae. The substitution position of $^{18}$F is not particularly limited.

General synthetic methods for the compounds of the present invention will be explained. However, synthetic methods of the compounds of the present invention are not limited to these methods. As the terminally-fluorinated alkyl fatty acids and the carboxylic acid having bis(trifluoromethyl)phenyl group as a partial structure of the compounds of the present invention, those ordinarily commercially available may be used, or they may be suitably synthesized depending on purposes. When the compounds are obtained by syntheses, corresponding alcohols and alkyl halides can be used as raw materials according to the method described by Richard C. Larock in Comprehensive Organic Transformations (VCH), the disclosure of which is expressly incorporated by reference herein in its entirety.

The aforementioned carboxylic acids can be condensed with steroid compounds, typically cholesterol or the like, and thereby introduced to the desired esters, or condensed with protected glycerol or glycerol derivatives such as 1,3-dihydroxyacetone, and thereby introduced to glyceride. In this process, a protective group can also be used, if necessary. As a protective group used in such a case, for example, any of the protective groups described by T. W. Green & P. G. M. Wuts in "Protecting Groups in Organic Synthesis" (John Wiley & Sons, Inc.), the disclosure of which is expressly incorporated by reference herein in its entirety, can be suitably selected and used.

After a suitable deprotection using the method described in "Protecting Groups in Organic Synthesis" (John Wiley & Sons, Inc.), the above-obtained glyceride can be reacted with suitable carboxylic acids, carboxylic halides, alkyl halides, phosphoric acid chlorides, phosphoric acid amide, or other phosphoric acid derivatives, and thereby introduced to the desired compound. The reaction may be conducted according, for example, to the method described by Richard C. Larock in Comprehensive Organic Transformations (VCH) as mentioned above.

The compound represented by each of the general formulae (Ia), (Ib), (Ic), (IIc), (Id), (IId), (Ie), and (IIe) wherein at least one of the fluorine atoms in the compound is $^{18}$F can be synthesized according, for example, to the method described in J. Labelled Compd. Radiopharm., 40, 11-13 (1997), the disclosure of which is expressly incorporated by reference herein in its entirety.

The compounds or the salts thereof of the present invention can be used as a membrane component of a liposome. When a liposome is prepared by using the compound or the salt thereof of the present invention, an amount of the compound or the salts thereof of the present invention is generally about from 5 to 90 mass %, preferably from 5 to 80 mass %, based on the total mass of membrane components. A single kind of the compound or the salt thereof of the present invention may be used, or two or more kinds may be used in combination.

As other membrane components of liposome, any of lipid compounds ordinarily used for the preparation of liposomes can be used. Such compounds are described in, for example, Biochim. Biophys. Acta, 150 (4), 44 (1982); Adv. in Lipid. Res., 16 (1) 1 (1978); "RESEARCH IN LIPOSOMES", P. Machy, L. Leserman, John Libbey EUROTEXT Co.); "Liposome" (Ed., Nojima, Sunamoto and Inoue, Nankodo), the disclosures of which are each expressly incorporated by reference herein in their entireties.

As the lipid compounds, phospholipids are preferred, and phosphatidylcholines (PC) are particularly preferred. Preferred examples of phosphatidylcholines include egg PC (PC derived from egg), dimyristoyl-PC (DMPC), dipalmitoyl-PC (DPPC), distearoyl-PC (DSPC), dioleyl-PC (DOPC) and the like. However, PCs are not limited to these examples.

In a preferred embodiment of the present invention, combination of a phosphatidylcholine and a phosphatidylserine (PS) can be used as membrane component of liposomes. Examples of the phosphatidylserine include those having lipid moieties similar to those of the phospholipids mentioned as preferred examples of the phosphatidylcholines. When a phosphatidylcholine and a phosphatidylserine are used in combination, molar ratio of PC and PS (PC:PS) used is preferably in the range of 90:10 to 10:90, more preferably in the range of 70:30 to 30:70

Another preferred embodiment of the liposome of the present invention includes a liposome containing a phosphatidylcholine and a phosphatidylserine and further containing a phosphoric acid dialkyl ester as membrane components. The two alkyl groups constituting the dialkyl ester of phosphoric acid are preferably the same kind of groups, and each alkyl group preferably contains 6 or more carbon atoms, more preferably 10 or more carbon atoms, still more preferably 12 or more carbon atoms. Preferred examples of the phosphoric acid dialkyl ester include, but not limited to, dilauryl phosphate, dimyristyl phosphate, dicetyl phosphate and the like. In the aforementioned embodiment, preferred amount of the phosphoric acid dialkyl ester is from 1 to 50 mass %, preferably from 1 to 30 mass %, further preferably from 1 to 20 mass %, based on the total mass of phosphatidylcholine and phosphatidylserine.

In the liposome containing a phosphatidylcholine, a phosphatidylserine, a phosphoric acid dialkyl ester, and the compound of the present invention or the salt thereof as membrane components, preferred mass ratios of PC, PS, phosphoric acid dialkyl ester, and the compound or the salt thereof of the present invention is from 5 to 50 mass %: from 5 to 50 mass %: from 1 to 10 mass %: from 1 to 80 mass %.

The components of the liposome of the present invention are not limited to the aforementioned four kinds of compounds, and other components may be admixed. Examples of such components include cholesterol, cholesterol esters, sphingomyelin, monosial ganglioside GM1 derivatives described in FEBS Lett., 223, 42 (1987); Proc. Natl. Acad. Sci., USA, 85, 6949 (1988), etc., the disclosures of which are each expressly incorporated by reference herein in their entireties, glucuronic acid derivatives described in Chem. Lett., 2145 (1989); Biochim. Biophys. Acta, 1148, 77 (1992), and the like, the disclosures of which are each expressly incorporated by reference herein in their entireties, polyethylene glycol derivatives described in Biochim. Biophys. Acta, 1029, 91 (1990); FEBS Lett., 268, 235 (1990), and the like, the disclosures of which are each expressly incorporated by reference herein in their entireties. However, the components are not limited to these examples.

The liposomes of the present invention can be prepared by any methods available in this field. Examples of the preparation methods are described in Ann. Rev. Biophys. Bioeng., 9, 467 (1980), "Liopsomes" (Ed. by M. J. Ostro, MARCELL DEKKER, INC.), the disclosures of which are each expressly incorporated by reference herein in their entireties, and the like, as well as the published reviews of liposomes mentioned above. More specifically, examples include the ultrasonication method, ethanol injection method, French press method, ether injection method, cholic acid method, calcium fusion method, freezing and thawing method, reverse phase evaporation method and the like. However, the preparation methods are not limited to these examples. Size of the liposome may be any of those obtainable by the aforementioned methods. Generally, the size in average may be 400 nm or less, preferably 200 nm or less. Structure of the liposome is not also particularly limited, and may be any structure such as unilamellar or multilamellar structure. It is also possible to add one or more kinds of appropriate medicaments or other contrast media inside the liposomes.

When the liposomes of the present invention are used as a contrast medium, they can be preferably administered parenterally, more preferably administered intravenously. For example, preparations in the form of an injection or a drip infusion can be provided as powdery compositions in a lyophilized form, and they can be used by being dissolved or resuspended just before use in water or an appropriate solvent (e.g., physiological saline, glucose infusion, buffering solution and the like). When the liposomes of the present invention are used as a contrast medium, a dose can be suitably determined so that the content of the compound in the liposomes becomes similar to that of a conventional contrast medium.

Although it is not intended to be bound by any specific theory, it is known that, in vascular diseases such as arteriosclerosis or restenosis after PTCA (percutaneous transluminal coronary angioplasty), vascular smooth muscle cells constituting tunica media of blood vessel abnormally proliferate and migrate into endosporium at the same time to narrow blood flow passages. Although triggers that initiate the abnormal proliferation of normal vascular smooth muscle cells have not yet been clearly elucidated, it is known that migration into endosporium and foaming of macrophages are important factors. It is reported that vascular smooth muscle cells then cause phenotype conversion (from constricted to composite type).

When the liposomes of the present invention are used, the compound serving as the defined contrast medium can be selectively taken up into the vascular smooth muscle cells abnormally proliferating under influences of foam macrophages. As a result, imaging becomes possible with high contrast between vascular smooth muscle cells of a lesion and a non-pathological site. Therefore, the contrast medium of the present invention can be suitably used particularly for imaging of vascular diseases. For example, contrast imaging of arteriosclerotic lesion or restenosis after PTCA can be performed.

Further, as described in, for example, J. Biol. Chem., 265, 5226 (1990), the disclosure of which is expressly incorporated by reference herein in its entirety, it is known that liposomes containing phospholipids, in particular, liposomes formed by using PC and PS, likely to accumulate on macrophages with the aid of scavenger receptors. Therefore, by using the liposomes of the present invention, the compounds of the present invention can be accumulated in a tissue or a lesion in which macrophages localize. If the liposomes of the present invention are used, the compound defined can be accumulated in macrophages in a larger amount compared with agents using a suspension or an oil emulsion according to a known technique.

Examples of tissues in which localization of macrophages is observed, which can be suitably imaged by the method of the present invention, include blood vessel, liver, spleen, air vesicle, lymph node, lymph vessel, and renal epithelium. Further, it is known that macrophages accumulate in lesions in certain classes of diseases. Examples of such diseases include tumor, arteriosclerosis, inflammation, infection and the like. Therefore, lesions of such diseases can be identified by using the liposomes of the present invention. In particular, it is known that foam macrophages, which take up a large amount of denatured LDL with the aid of scavenger receptors, accumulate in atherosclerosis lesions at an early stage (Am. J. Pathol., 103, 181 (1981); Annu. Rev. Biochem., 52, 223 (1983), the disclosures of which are each expressly incorporated by reference herein in their entireties). Therefore, by performing MRI after accumulation of the liposomes of the present invention in the macrophages, it is possible to identify locations of atherosclerosis lesions at an early stage, which is hardly achievable by other means.

The contrast imaging method using the liposomes of the present invention is not particularly limited. For example, contrast imaging methods using the liposomes as a contrast medium for MRI imaging can be conducted by measuring nuclear spin of fluorine atom. It is also possible to use the liposome as a contrast medium for PET by using radioisotope such as $^{18}$F.

EXAMPLES

The present invention will be explained more specifically with reference to the following examples. However, the scope of the present invention is not limited to the following examples. The compound numbers used in the following examples correspond to the numbers of the exemplified compounds mentioned above. The structures of the compounds mentioned in the examples were confirmed on the basis of NMR spectra and mass spectra.

Preparation of Compound a2-6

6-(Perfluorohexyl) hexanol (6.32 g) was dissolved in dichloromethane (60 mL). The solution was added with triethylamine (3.15 mL) and stirred at 0° C. The solution was further added dropwise with methanesulfonyl chloride (1.28 mL), and stirred after warmed up to room temperature. The reaction solution was added with saturated sodium hydrogen carbonate, and extracted twice with dichloromethane. The resulting organic layer was washed with 1N aqueous hydrochloric acid and saturated brine. After the organic layer was dried over anhydrous magnesium sulfate, the solvent was removed to obtain the corresponding sulfonic acid ester (7.31 g)(98%).

Sodium hydride (oil dispersion, 60%, 0.71 g) was added with dimethylformamide (DMF) (25 mL), and the mixture was stirred at 0° C. Diethyl malonate (2.82 g) dissolved in DMF (3 mL) was added dropwise to the mixture, and the mixture was warmed up to room temperature. The mixture was added dropwise with the above sulfonic acid ester (7.31 g) dissolved in DMF (10 mL), and stirred at room temperature for two hours, and at 80° C. for two hours. The reaction solution was added with 1N aqueous hydrochloric acid, and extracted twice with dichloromethane. The resulting organic layer was washed with saturated brine. After the organic layer was dried over anhydrous magnesium sulfate, the solvent was removed and the residue was purified by silica gel column chromatography to obtain the corresponding malonic acid derivative (4.83 g, 58%).

The above malonic acid derivative (4.83 g) was dissolved in ethanol (70 mL). The solution was added with lithium hydroxide (0.62 g), and stirred at room temperature. The reaction was stopped by adding 3N hydrochloric acid (1.2 mL) to the reaction solution. The reaction solution was added with dichloromethane and 1N aqueous hydrochloric acid, and extracted twice with dichloromethane. After the organic layer was dried over anhydrous sodium sulfate, the solvent was removed. The residue was dissolved in pyridine (20 mL), and added with a concentrated hydrochloric acid. The solution was stirred at 130° C. for three hours. The reaction solution was added with dichloromethane and 1N aqueous hydrochloric acid, and extracted twice with dichloromethane. The organic layer was dried over anhydrous magnesium sulfate. The solvent was then removed, and the residue was purified by silica gel column chromatography to obtain the corresponding carboxylic acid (3.55 g, 89%).

The above carboxylic acid (0.20 g) was dissolved in dichloromethane (3 mL). The mixture was added with cholesterol (0.19 g), 4-(dimethylamino)pyridine (7 mg), and WSC (Dojindo)(0.11 g), and stirred at room temperature. The reaction solution was added with water, extracted twice with dichloromethane. The resulting organic layer was dried over anhydrous magnesium sulfate. The solvent was then removed, and the residue was purified by silica gel column chromatography to obtain Compound a2-6 (0.29 g, 81%).

$^1$H-NMR (300 MHz, CDCl$_3$) δ 5.38 (1H, d), 4.70-4.53 (1H, m), 2.34-0.80 (59H, m), 0.70 (3H, s).

Preparation of Compound b1-1

Cholesterol chloroformate (0.91 g) was dissolved in dichloromethane (5 mL). The solution was added with 3,5-bis(trifluoromethyl)phenol (0.52 g) and pyridine (0.32 g), and stirred at room temperature. The reaction solution was added with 1N aqueous hydrochloric acid, and extracted twice with dichloromethane. The resulting organic layer was washed with saturated sodium hydrogen carbonate and saturated brine. After the organic layer was dried over anhydrous magnesium sulfate, the solvent was removed, and the residue was purified by silica gel column chromatography to obtain Compound b1-1 (0.92 g, 71%).

$^1$H-NMR (300 MHz, CDCl$_3$) δ: 7.51 (1H, s), 7.32 (2H, s), 5.39 (1H, d), 4.83-4.68 (1H, m), 4.69 (2H, s), 2.34 (2H, d), 2.06-0.80 (38H, m), 0.70 (3H, s).

Preparation of Compound b1-2

Cholesterol chloroformate (0.94 g) was dissolved in DMF (5 mL). The solution was added with potassium carbonate (0.56 g) and 3,5-bis(trifluoromethyl)phenol (0.92 g), and stirred at 60° C. for 5 hours. The reaction solution was added with water, and extracted with ethyl acetate. The resulting organic layer was washed with saturated ammonium chloride solution and saturated brine. After the organic layer was dried over anhydrous magnesium sulfate, the solvent was removed, and the residue was purified by silica gel column chromatography to obtain Compound b1-2 (1.13 g, 85%).

$^1$H-NMR (300 MHz, CDCl$_3$) δ: 7.78 (1H, s), 7.70 (2H, s), 5.44 (1H, d), 4.70-4.53 (1H, m), 2.50 (2H, d), 2.10-0.80 (38H, m), 0.70 (3H, s).

Preparation of Compound b1-8

3,5-Bis(trifluoromethyl) phenol (20.6 g) was dissolved in 1N sodium hydroxide (270 mL). The solution was refluxed under heating for 10 hours. Further, the solution was added with 11-bromododecanoic acid (4.7 g). After the reflux under heating was continued, the reaction solution was left to be cooled. The reaction solution was added with 1N aqueous hydrochloric acid and extracted with ethyl acetate. The resulting organic layer was dried over anhydrous magnesium sulfate, and the solvent was removed. The resulting crystals was washed with hexane and purified by silica gel column chromatography to obtain 11-(3,5-Bis(trifluoromethyl) phenoxy) dodecanoic acid (18.4 g, 50%).

The above carboxylic acid (0.65 g) was dissolved in dichloromethane (3 mL). The mixture was added with cholesterol (0.61 g), 4-(dimethylamino)-pyridine (19 mg), and WSC (Dojindo)(0.37 g), and stirred at room temperature. The reaction solution was added with water, and extracted twice with ethyl acetate. The resulting organic layer was washed with saturated brine. After the organic layer was dried over anhydrous magnesium sulfate, the solvent was removed and the residue was purified by silica gel column chromatography to obtain Compound b1-8 (0.76 g, 62%).

$^1$H-NMR (300 MHz, CDCl$_3$) δ: 7.44 (1H, s), 7.29 (2H, s), 5.38 (1H, d), 4.65-4.56 (1H, m), 4.01 (2H, t), 2.31 (2H, d), 2.28 (2H, t), 2.10-0.80 (54H, m), 0.70 (3H, s).

Preparation of Compound b4-2

Cholesterol succinate (0.98 g) was dissolved in dichloromethane (5 mL). The mixture was added with 3,5-bis(trifluoromethyl) phenol (0.55 g), 4-(dimethylamino)pyridine (28 mg), and WSC (Dojindo)(0.52 g), and stirred at room temperature. The reaction solution was added with water, and extracted twice with dichloromethane. The resulting organic layer was washed with saturated brine. After the organic layer was dried over anhydrous magnesium sulfate, the solvent was removed and the residue was purified by silica gel column chromatography to obtain Compound b4-2 (0.64 g, 46%).

$^1$H-NMR (300 MHz, CDCl$_3$) δ: 7.76 (1H, s), 7.61 (2H, s), 5.37 (1H, d), 4.73-4.60 (1H, m), 2.91 (2H, dd), 2.74 (2H, dd), 2.33 (2H, d), 2.28 (2H, t), 2.10-0.80 (38H, m), 0.70 (3H, s).

Preparation of Compound c1-5

6-(Perfluorohexyl) hexanol (6.32 g) was dissolved in dichloromethane (60 mL). The solution was added with triethylamine (3.15 mL) and stirred at 0° C. The solution was further added dropwise with methanesulfonyl chloride (1.28 mL), and warmed to room temperature and stirred. The reaction solution was added with saturated sodium hydrogen carbonate, and extracted twice with dichloromethane. The resulting organic layer was washed with 1N aqueous hydrochloric acid and saturated brine. After the organic layer was dried over anhydrous magnesium sulfate, the solvent was removed to obtain the corresponding sulfonic acid ester (7.31 g, 98%).

Sodium hydride (oil dispersion, 60%, 0.71 g) was added with dimethylformamide (DMF) (25 mL), and the mixture was stirred at 0° C. Diethyl malonate (2.82 g) dissolved in DMF (3 mL) was added dropwise to the mixture, and the mixture was warmed up to room temperature. The mixture was added dropwise with the above sulfonic acid ester (7.31 g) dissolved in DMF (10 mL), and stirred at room temperature for two hours, and at 80° C. for two hours. The reaction solution was added with 1N aqueous hydrochloric acid, and extracted twice with dichloromethane. The resulting organic layer was washed with saturated brine. After the organic layer was dried over anhydrous magnesium sulfate, the solvent was removed and the residue was purified by silica gel column chromatography to obtain the corresponding malonic acid derivative (4.83 g, 58%).

The above malonic acid derivative (4.83 g) was dissolved in ethanol (70 mL). The solution was added with lithium hydroxide (0.62 g), and stirred at room temperature. The reaction was stopped by adding 3N hydrochloric acid (1.2 mL) to the reaction solution. The reaction solution was added with dichloromethane and 1N aqueous hydrochloric acid, and extracted twice with dichloromethane. After the organic layer was dried over anhydrous sodium sulfate, the solvent was removed. The residue was dissolved in pyridine (20 mL), added with a concentrated hydrochloric acid. The solution was stirred at 130° C. for three hours. The reaction solution was added with dichloromethane and 1N aqueous hydrochloric acid, and extracted twice with dichloromethane. After the organic layer was dried over anhydrous magnesium sulfate, the solvent was removed and the residue was purified by silica gel column chromatography to obtain the corresponding carboxylic acid (3.55 g, 89%).

Sodium hydride (0.8 g) was added with DMF (5 mL) and tetrahydrofuran (THF) (20 mL), and the solution was stirred at 0° C. The solution was added dropwise with a solution of (S)-(+)-2,2-dimethyl-1,3-dioxolan-4-methanol (2.4 g) in a mixture of DMF (3 mL) and THF (3 mL), and stirred at 0° C. for one hour. The solution was added with 4-methoxybenzyl chloride (2.8 mL), and stirred at room temperature for three hours. The solution was added with saturated ammonium chloride, and extracted twice with ethyl acetate. The resulting organic layer was washed four times with water and ones with saturated brine. After the organic layer was dried over anhydrous magnesium sulfate, the solvent was removed to obtain a crude product of (S)-(+)-4-(4-methoxybenzyloxymethyl)-2,2-dimethyl-1,3-dioxolane (4.1 g, 89%).

The crude product of (S)-(+)-4-(4-methoxybenzyloxymethyl)-2,2-dimethyl-1,3-dioxolane (4.1 g) was dissolved in methanol (10 mL). The solution was added with 1N hydrochloric acid and stirred at room temperature for one day. The solution was adjusted to pH 6 by addition of saturated aqueous sodium hydrogen carbonate, and extracted four times with dichloromethane. After the organic layer was dried over anhydrous sodium sulfate, the solvent was removed and the residue was purified by silica gel column chromatography to obtain (R)-(+)-3-(4-methoxybenzyloxy)-1,2-propanediol (2.4 g, 69%).

(R)-(+)-3-(4-Methoxybenzyloxy)-1,2-propanediol (0.61 g) was dissolved in dichloromethane (4 mL). The solution was added with the above-obtained carboxylic acid (2.63 g), dimethylaminopyridine (69 mg), and ethyldimethylaminopropyl carbodiimide hydrochloride (1.25 g), and stirred at room temperature for two days. The reaction solution was added with water, extracted twice with dichloromethane. After the resulting organic layer was dried over anhydrous magnesium sulfate, the solvent was removed and the residue was purified by silica gel column chromatography to obtain 1,2-diglyceride (2.33 g, 74%).

The above 1,2-diglyceride (1.79 g) was added with dichloromethane (25 mL) and water (2.5 mL), and further added with 2,3-dichloro-5,6-dicyano-1,4-benzoquinone (0.55 g), and the solution was vigorously stirred at room temperature for two hours. After addition of 1N sodium hydroxide, the solution was extracted with ethyl acetate. The resulting organic layer was washed with saturated ammonium chloride and saturated brine. After the organic layer was dried over anhydrous sodium sulfate, the solvent was removed and the residue was purified by silica gel column chromatography to obtain deprotected 1,2-diglyceride (1.26 g, 79%).

Boc-Ser-O$^t$Bu (0.34 g) was dissolved in dichloromethane (5 mL), added with triethylamine (0.40 g), and the solution was stirred at 0° C. The solution was added with N,N-diisopropylmethyl phosphonic amide chloride (0.32 mL), and stirred at 0° C. for 20 minutes. The solution was added with ice-cooled saturated aqueous sodium hydrogen carbonate, and extracted twice with dichloromethane. After the resulting organic layer was dried over anhydrous sodium sulfate, the solvent was removed.

The residue was added with the above 1,2-diglyceride (1.26 g) dissolved in dichloromethane (20 mL). The solution was added with tetrazole (0.13 g) and stirred at room temperature for 20 minutes, and then added with saturated brine. The solution was extracted twice with dichloromethane. After the resulting organic layer was dried over anhydrous sodium sulfate, the solvent was removed and the residue was purified by silica gel column chromatography to obtain phosphoric acid triester (1.22 g, 71%).

The above phosphoric acid triester (1.22 g) was dissolved in methylethyl ketone (10 mL), and the solution was added with sodium iodide (0.70 g), and refluxed under heating for 30 minutes. The reaction solution was added with 1N hydrochloric acid, and extracted with mixture solution of chloroform/methanol (5/1). After the resulting organic layer was dried over anhydrous sodium sulfate, the solvent was removed to obtain phosphoric acid diester (1.15 g, 95%).

The above phosphoric acid diester (1.15 g) was added with hydrochloric acid/dioxane solution (to 4 mol/L, 4 mL), and stirred at room temperature. The solvent was evaporated and the residue was recrystallized three times by addition of acetonitrile to obtain Compound c1-5 (0.92 g, 91%).

$^1$H-NMR (400 MHz, CD$_3$OD) δ: 5.30-5.20 (1H, m), 4.43 (1H, dd), 4.40-4.27 (3H, m), 4.18 (1H, dd), 4.12-4.00 (2H, m), 2.36 (4H, dt), 2.28 (2H, t), 2.13 (4H, ddd), 1.70-1.28 (20H, m).

Mass (MALDI-TOFF): m/z (α-cyano-4-hydroxycinnamic acid) 1170 (M+Na); 1146 (M-H)

Preparation of Compound d1-6

3,5-Bis(trifluoromethyl) phenol (20.6 g) was dissolved in 1N sodium hydroxide (270 mL). The solution was refluxed under heating for 10 hours. After addition of 11-bromododecanoic acid (4.7 g), the solution was kept refluxed under heating, and then left to be cooled. The reaction solution was added with 1N aqueous hydrochloric acid and extracted with ethyl acetate. The resulting organic layer was dried over anhydrous magnesium sulfate, and the solvent was removed. The resulting crystals was washed with hexane and purified by silica gel column chromatography to obtain 11-(3,5-bis(trifluoromethyl) phenoxy)dodecanoic acid (18.4 g, 50%).

Sodium hydride (0.8 g) was added with DMF (5 mL) and tetrahydrofuran (THF) (20 mL), and the solution was stirred at 0° C. The solution was added dropwise with a solution of (S)-(+)-2,2-dimethyl-1,3-dioxolan-4-methanol (2.4 g) in a mixture of DMF (3 mL) and THF (3 mL), and stirred at 0° C. for one hour. The solution was added with 4-methoxybenzyl chloride (2.8 mL), and stirred at room temperature for 3 hours. The solution was added with saturated ammonium chloride, and extracted twice with ethyl acetate. The resulting organic layer was washed four times with water and ones with saturated brine. After the organic layer was dried over anhydrous magnesium sulfate, the solvent was removed to obtain a crude product of (S)-(+)-4-(4-methoxybenzyloxymethyl)-2,2-dimethyl-1,3-dioxolane (4.1 g, 89%).

The crude product of (S)-(+)-4-(4-methoxybenzyloxymethyl)-2,2-dimethyl-1,3-dioxolane (4.1 g) was dissolved in methanol (10 mL). The solution was added with 1N hydrochloric acid and stirred at room temperature for one day. The solution was adjusted to pH 6 by addition of saturated sodium hydrogen carbonate, and extracted four times with dichloromethane. After the organic layer was dried over anhydrous sodium sulfate, the solvent was removed and the residue was purified by silica gel column chromatography to obtain (R)-(+)-3-(4-methoxybenzyloxy)-1,2-propanediol (2.4 g, 69%).

(R)-(+)-3-(4-Methoxybenzyloxy)-1,2-propanediol (0.35 g) was dissolved in dichloromethane (3 mL). The solution was added with 11-(3,5-bis(trifluoromethyl) phenoxy)dodecanoic acid (1.37 g), dimethylaminopyridine (23 mg), and ethyldimethylaminopropyl carbodiimide hydrochloride (0.76 g), and stirred at room temperature for two days. The reaction solution was added with water, and extracted twice with dichloromethane. After the resulting organic layer was dried over anhydrous magnesium sulfate, the solvent was removed and the residue was purified by silica gel column chromatography to obtain 1,2-diglyceride (1.23 g, 74%).

The above 1,2-diglyceride (1.23 g) was added with dichloromethane (20 mL) and water (2 mL), and further added with 2,3-dichloro-5,6-dicyano-1,4-benzoquinone (0.42 g), and the solution was vigorously stirred at room temperature for two hours. After addition of 1N sodium hydroxide, the solution was extracted with ethyl acetate. The resulting organic layer was washed with saturated ammonium chloride and saturated brine. After the organic layer was dried over anhydrous sodium sulfate, the solvent was removed and the residue was purified by silica gel column chromatography to obtain deprotected-1,2-diglyceride (0.69 g, 64%).

The above 1,2-diglyceride (0.69 g) is dissolved in dichloromethane (2 mL). To the solution, morpholino acetic acid (0.14 g) which was prepared according to the method described in J. Mol. Struct., 560(1-2), 261 (2001), the disclosure of which is expressly incorporated by reference herein in its entirety, and dimethylaminopyridine (10 mg) were added. Further, the solution was added with 1-ethyl-dimethylaminopropyl carbodiimide hydrochloride (EDC-HCl, 0.22 g), and stirred at room temperature for one day. The reaction solution was added with water and extracted twice with chloroform. After the resulting organic layer was dried over anhydrous sodium sulfate, the solvent was removed and the residue was purified by silica gel column chromatography to obtain Compound d1-6 (0.65 g, 82%).

$^1$H-NMR (300 MHz, CDCl$_3$): 7.43 (2H, s), 7.29 (4H, s), 5.32-5.24 (1H, m), 4.39 (1H, dd), 4.29 (1H, dd), 4.20 (1H, dd), 4.14 (1H, dd), 4.03 (4H, t), 3.76-3.72 (4H, m), 3.22 (2H, s), 2.60-2.55 (4H, m), 2.30 (4H, dt), 1.88-1.65 (4H, m), 1.70-1.22 (28H, m).

Preparation of Compound d1-2

Ethyl 7-bromoheptanoate and 3,5-bis(trifluoromethyl) phenol were added to dimethylformamide (DMF). The solution was added with potassium carbonate and stirred at room temperature. The solution was added with water and extracted twice with ethyl acetate. After the organic layer was washed three times with water and dried over anhydrous magnesium sulfate, the solvent was removed. The residue was purified by silica gel column chromatography to obtain ethyl 7-(3,5-bis(trifluoromethyl)phenoxy)heptanoate.

Ethyl 7-(3,5-bis(trifluoromethyl)phenoxy)heptanoate was added to 95% ethanol and dissolved by reflux. The solution was then added with sodium hydroxide and further refluxed. The resulting crystals were filtered, washed with ethanol, and then added with dichloromethane and 1N hydrochloric acid. The solution was extracted twice with dichloromethane. After the organic layer was dried over anhydrous magnesium sulfate, the solvent was removed and the residue was purified by silica gel column chromatography to obtain 7-(3,5-bis(trifluoromethyl) phenoxy) heptanoic acid.

Compound d1-2 can be obtained in a similar manner to that of the preparation of the above Compound d1-6, except 7-(3,5-bis(trifluoromethyl)phenoxy)heptanoic acid is used instead of 11-(3,5-bis(trifluoromethyl)phenoxy)dodecanoic acid.

Preparation of Compound d1-4

Methyl 9-hydroxynonanoate and pyridine were added to dichloromethane. The solution was stirred at 0° C., added with methanesulfonyl chloride, and further stirred with gradually warming up to room temperature. The solution was added with water, and extracted twice with dichloromethane. The resulting organic layer was washed with 1N hydrochloric acid and saturated sodium hydrogen carbonate. After the organic layer was dried over anhydrous sodium sulfate, the solvent was removed and the residue was purified by silica gel column chromatography to obtain methyl 9-(methanesulfonyloxy)nonanoate.

9-(3,5-Bis(trifluoromethyl)phenoxy) nonanoic acid was obtained in a similar manner to that of the preparation of 7-(3,5-bis(trifluoromethyl)phenoxy) heptanoic acid, except methyl 9-(methanesulfonyloxy) nonanoate is used instead of ethyl 7-bromoheptanoate.

Compound d1-4 was obtained in a similar manner to that of the preparation of the above Compound d1-6, except 9-(3,5-Bis(trifluoromethyl)phenoxy) nonanoic acid was used instead of 11-(3,5-bis(trifluoromethyl)phenoxy)dodecanoic acid.

Preparation of Compound d1-8

Monomethyl tridecanedioate was obtained by using tridecanedioic acid according to the method described in Synth. Commun., 17, 1339 (1987). Further, methyl 13-hydroxytridecanoate was obtained by using monomethyl tridecanedioate according to the method described in Aust. J. Chem., 48, 1893 (1995).

13-(3,5-Bis(trifluoromethyl)phenoxy)tridecanoic acid was obtained in a similar manner to that of the preparation of 9-(3,5-bis(trifluoromethyl)phenoxy) nonanoic acid, by using methyl 13-hydroxytridecanoate.

Compound d1-8 was obtained in a similar manner to that of the preparation of the above Compound d1-6, except 13-(3,5-bis(trifluoromethyl)phenoxy)tridecanoic acid was used instead of 11-(3,5-bis(trifluoromethyl)phenoxy)dodecanoic acid.

Preparation of Compound d1-10

21-(3,5-Bis(trifluoromethyl)phenoxy)heneicosanoic acid was obtained by increasing two carbons according to the method described in Arch. Pharm. (Weinheim) 328, 271 (1995) by using 19-(3,5-Bis(trifluoromethyl)phenoxy)nanodecanoic acid and diethyl malonate.

Compound d1-10 was obtained in a similar manner to that of the preparation of the above Compound d1-6, except 21-(3,5-bis(trifluoromethyl)phenoxy) heneicosanoic acid was used instead of 1-(3,5-bis(trifluoromethyl) phenoxy)dodecanoic acid.

Preparation of Compound d2-1

Morpholine and succinic acid anhydride were dissolved in ethyl acetate and the solution was refluxed. The solvent was evaporated to obtain a crude product of morpholino succinic acid Compound d2-1 was obtained in a similar manner to that of the preparation of the above Compound d1-6, except the crude product was used instead of morpholino acetic acid.

Preparation of Compound d2-2

Succinic acid anhydride (0.15 g) and 1,2-glyceride which was used in the preparation of Compound d1-6 were dissolved in dichloromethane. The solution was added with pyridine and dimethylaminopyridine and refluxed. After the reaction solution was concentrated, the residue was purified to obtain Compound d2-2.

Preparation of Compound d2-3

Compound d2-3 can be obtained by using Compound d2-2 and triethylene glycol monoethyl ether via a condensation reaction using EDC HCl which was used in the preparation of Compound d1-6.

Preparation of Compound d2-4

Compound d2-4 can be obtained by using Compound d2-2 and 25% aqueous ammonia via a condensation reaction using EDC HCl which was used in the preparation of Compound d1-6.

Preparation of Compound d2-5

Compound d2-5 can be obtained by using Compound d2-2 according to the method described in J. Med. Chem., 40, 3381 (1997), the disclosure of which is expressly incorporated by reference herein in its entirety.

Preparation of Compound d2-6

Compound d2-6 (n=2, 3, 4, 5) can be obtained in a similar manner to that of the preparation of the above Compound d1-6, except 3-morpholinopropanoic acid, 4-morpholinobutanoic acid, 5-morpholinopentanoic acid, and 6-morpholinohexanoic acid, which are prepared according to the method described in J. Mol. Struct., 560(1-2), 261 (2001), are used respectively instead of morpholino acetic acid.

Preparation of Compound d2-7

Compound d2-7 can be obtained in a similar manner to that of the preparation of the above Compound d1-6, except acetic acid is used instead of morpholino acetic acid.

Preparation of Compound d2-8

Compound d2-8 can be obtained in a similar manner to that of the preparation of the above Compound d1-6, except N,N-dimethylglycine is used instead of morpholino acetic acid.

Preparation of Compound d2-11

2,2-Dimethyl-1,3-dioxolane-4-methanol was dissolved in tetrahydrofuran, and the solution was stirred at 0° C. The solution was slowly added with 60% sodium hydride, stirred with the temperature raised to room temperature, and stirred continuously. The solution was again cooled to 0° C., added with chloroacetyl morpholine dissolved in tetrahydrofuran, and stirred at room temperature. The solution was added with water, and extracted twice with ethyl acetate. The resulting organic layer was washed once with saturated brine. After the organic layer was dried over anhydrous magnesium sulfate, the solvent was removed to obtain a morpholine-substituted glycerol derivative.

The above glycerol derivative was added with dioxane hydrochloric acid solution (to 4 mol/L) and stirred. After the reaction was completed, the solvent was removed to obtain the desired diol as a crude product.

Compound d2-11 was obtained by using the above diol and 11-(3,5-bis((trifluoromethyl)phenoxy)dodecanoic acid according to the method described in J. Med. Chem., 29(12), 2457 (1986), the disclosure of which is expressly incorporated by reference herein in its entirety.

Preparation of Compound d2-12 t-Butyl-protected form of Compound d2-12 was obtained in a similar manner to that of the preparation of the above Compound d2-11, except t-butyl bromoacetate was used instead of chloroacetyl morpholine. The above protected form was dissolved in dichloromethane. The solution was added with trifluoroacetic acid and stirred at room temperature. The reaction solution was added with water and chloroform and extracted three times. After the resulting organic layer was dried over sodium sulfate, the solvent was removed. The residue was purified by silica gel column chromatography to obtain Compound d2-12.

Preparation of Compound d2-9

Cis-1,3-O-benzylideneglycerol was dissolved in tetrahydrofuran, and the solution was stirred at 0° C. The solution was slowly added with 60% sodium hydride, stirred with the temperature raised to room temperature, and stirred continuously. The solution was again cooled to 0° C., added with ethyl bromoacetate dissolved in tetrahydrofuran (3 mL), and stirred at room temperature. The solution was added with saturated ammonium chloride, and extracted twice with ethyl acetate. The resulting organic layer was washed once with saturated brine. After the organic layer was dried over anhydrous magnesium sulfate, the solvent was removed and the residue was purified by silica gel column chromatography to obtain a glycerol-substituted acetic acid derivative.

The above glycerol-substituted acetic acid derivative is dissolved in ethanol and the solution was added with water and sodium hydroxide, and refluxed under heating. After cooled to room temperature, the solution was adjusted to pH 1 to 2 by using 1N hydrochloric acid, and extracted three times with chloroform. After the organic layer was dried over anhydrous magnesium sulfate, the solvent was removed to obtain the desired carboxylic acid.

Acetal protected form of Compound d2-9 was obtained in a similar manner to that of the preparation of the above Compound d1-6, except the above carboxylic acid was used instead of morpholino acetic acid. Further, the deprotection reaction using acid similar to that for Compound d2-12 was conducted to obtain Compound d2-9.

Preparation of Compound d2-13

Compound d2-13 can be obtained in a similar manner to that of the preparation of the above Compound d1-6, except 2-furan carboxylic acid is used instead of morpholino acetic acid.

Preparation of Compound d2-14

Compound d2-14 can be obtained in a similar manner to that of the preparation of the above Compound d1-6, except tetrahydro-2-furan carboxylic acid is used instead of morpholino acetic acid.

Preparation of Compound d2-15

Compound d2-15 can be obtained in a similar manner to that of the preparation of the above Compound d1-6, except tetrahydro-3-furan carboxylic acid is used instead of morpholino acetic acid.

Preparation of Compound d2-17

Compound d2-17 can be obtained by using Compound d2-12 and 25% aqueous ammonia via a condensation reaction using EDC-HCl which was used in the preparation of Compound d1-6.

Preparation of Compound d2-18

Triethylene glycol monoethyl ether was dissolved in tetrahydarofuran and the solution was added with tosyl chloride. The solution was cooled to 0° C., added with triethylamine, and stirred at 0° C. and room temperature. The reaction solution was added with 1N hydrochloric acid and ethyl acetate, and extracted twice with ethyl acetate. After the organic layer was dried over anhydrous sodium sulfate, the solvent was removed. The residue was purified by silica gel column chromatography to obtain the desired tosyl.

Compound d2-18 was obtained in a similar manner to that of the preparation of the above Compound d2-11, except the above tosyl was used instead of chloroacetyl morpholine.

Preparation of Compound d2-19

2-(Cis-1,3-O-benzylideneglyceroyl)ethanol was prepared according to the method described in Arch. Pharm. (Weinheim), 328, 271 (1995), which was then protected with t-butyldimethylsilyl (TBS) protective group according to the method described in "Protecting groups in organic synthesis" (John Wiley & sons, inc.) written by T. W. Green & P. G. M. Wuts. TBS-protected form of Compound d2-19 was obtained in a similar manner to that of the preparation of the above Compound d2-11, except the above TBS-protected form of 2-(cis-1,3-O-benzylideneglycerol) ethanol was used instead of chloroacetyl morpholine. Further, Compound d2-19 was obtained by deprotection of TBS group according to the method described in the above "Protecting groups in organic synthesis".

Preparation of Compound d2-20

1,2-Glyceride which was used in the preparation of Compound d1-6 was dissolved in N,N-dimethylformamide, and the solution was stirred at 0° C. After addition of sodium hydride, the solution was warmed up to room temperature, added with 1,3-propane sultone, and kept stirred. The reaction solution was added with 1N hydrochloric acid, and extracted three times with dichloromethane. After the resulting organic layer was dried over anhydrous magnesium sulfate, the solvent was removed to obtain Compound d2-20.

Preparation of Compound d3-6

The above 1,2-glyceride (1.78 g) was dissolved in tetrahydrofuran (10 mL). The solution was added with 2-chloro-1,3,2-dioxaphosphorane-2-oxide (0.72 g), and stirred at 0° C. After addition of triethylamine (0.84 mL), the solution was warmed up to room temperature, and stirred for 8 hours. Again, the solution was cooled to 0° C., added with 2-chloro-1,3,2-dioxaphosphorane-2-oxide (0.29 g), and triethylamine (0.28 mL), and stirred at room temperature. After the resulting inorganic salt was separated by filtration and washed with tetrahydrofuran, the solvent was removed. The residue was dissolved in tetrahydrofuran (5 mL). The solution was added with triethylamine (3 mL) dissolved in acetonitrile (20 mL), set under seal, and stirred at 70° C. for 15 hours. After the solution was left to be cooled, the resulting crystals are separated by filtration, and the solvent of the resulting solution was removed. The residue was added with ethyl acetate/acetonitrile mixture solution, and the resulting crystals are separated by filtration. The solvent of the resulting solution was removed, and the residue was purified by silica gel column chromatography to obtain Compound d3-6 (0.94 g, 45%).

$^1$H-NMR (300 MHz, CDCl$_3$) δ: 7.46 (2H, s), 7.42 (4H, s), 5.30-5.20 (1H, m), 4.42 (1H, dd), 4.35 (2H, bs), 4.34 (1H, dd), 4.18 (1H, dd), 4.08 (1H, dd), 4.06 (4H, t), 3.83 (2H, bs), 3.39 (9H, s), 2.34 (4H, dt), 1.80 (4H, quin), 1.65-1.24 (28H, m).

Preparation of Compound d4-6

Boc-Ser-O$^t$Bu (0.38 g) was dissolved in dichloromethane (5 mL). The solution was added with triethylamine (0.45 g) and stirred at 0° C. The solution was added with N,N-diisopropylmethyl phosphonamide chloride (0.37 mL), and stirred at 0° C. for 20 minutes. The solution was added with ice-cooled saturated aqueous sodium hydrogen carbonate, and extracted twice with dichloromethane. The resulting organic layer was dried over anhydrous sodium sulfate, and the solvent was removed.

The residue was added with the above 1,2-glyceride (1.30 g) dissolved in dichloromethane (20 mL). The solution was added with tetrasol (0.14 g) and stirred at room temperature for one hour. The reaction solution was added with aqueous hydrogen peroxide (31%, 0.5 mL), stirred at room temperature for 20 minutes, and added with saturated brine. The solution was extracted twice with dichloromethane. After the resulting organic layer was dried over anhydrous sodium sulfate, the solvent was removed. The residue was purified by silica gel column chromatography to obtain the phosphate triester (1.22 g, 69%).

The above phosphate triester (1.22 g) was dissolved in methylethylketone (10 mL). The solution was added with sodium iodide (0.74 g) and refluxed under heating for 30 minutes. The reaction solution was added with 1N hydrochloric acid, extracted with chloroform/methanol (5/1). After the resulting organic layer was dried over anhydrous sodium sulfate, the solvent was removed to obtain the phosphate diester (1.17 g, 97%).

The above phosphate diester (1.17 g) was added with hydrochloric acid/dioxane solution (to 4 mol/L, 4 mL) and the solution was stirred at room temperature. The solvent was evaporated. The residue was recrystallized three times by addition of acetonitrile to obtain Compound d4-6 (0.80 g, 78%).

¹H-NMR (300 MHz, CD₃OD) δ: 7.46 (2H, s), 7.42 (4H, s), 5.30-5.20 (1H, m), 4.42 (1H, dd), 4.40-4.25 (3H, m), 4.21-4.00 (4H, m), 4.08 (4H, t), 2.34 (4H, dt), 1.80 (4H, quin), 1.65-1.24 (28H, m).

Mass (MALDI-TOF): m/z (α-cyano-4-hydroxycinnamic acid) 1074 (M+Na); 1050 (M-H)

Preparation of Compound d5-6

1,3-Dihydroxyacetone (dimer, 225 mg) was dissolved in dichloromethane (10 mL). The solution was added with 11-(3,5-bis(trifluoromethyl)phenoxy)dodecanoic acid (2.08 g), dimethylaminopyridine (32 mg), and ethyldimethylaminopropyl carbodiimide hydrochloride (1.22 g), and stirred at room temperature for three hours. After the reaction solution was concentrated, the residue was purified by silica gel column chromatography to obtain the diester (0.88 g, 40%).

The above diester (0.88 g) was dissolved in tetrahydrofuran (10 mL). The solution was added with 1 mL of water and stirred at 0° C. The solution was gradually added with sodium borohydride (56 mg) and kept stirred at 0° C. for one hour. After addition of saturated ammonium chloride, the solution was extracted twice with dichloromethane. The resulting organic layer was washed with saturated brine. After the organic layer was dried over sodium sulfate, the solvent was evaporated. The residue was purified by silica gel column chromatography to obtain 1,3-diglyceride (0.75 g, 85%).

Compound d5-6 was obtained in a similar manner to that of Compound d1-6, except that the above 1,3-diglyceride was used instead of 1,2-diglyceride.

¹H-NMR (300 MHz, CDCl₃) δ: 7.43 (2H, s), 7.29 (4H, s), 5.36-5.27 (1H, m), 4.32 (2H, dd), 4.14 (2H, dd), 4.03 (4H, t), 3.78-3.72 (4H, m), 3.24 (2H, s), 2.62-2.55 (4H, m), 2.30 (4H, t), 1.88-1.76 (4H, m), 1.70-1.22 (28H, m).

Preparation of Compound d6-2

Compound d6-2 was obtained in a similar manner to that of Compound d3-6, except that the above 1,3-diglyceride was used instead of 1,2-diglyceride.

¹H-NMR (300 MHz, CDCl₃) δ: 7.42 (2H, s), 7.28 (4H, s), 4.58-4.46 (1H, m), 4.35 (2H, bs), 4.26 (4H, dd), 4.03 (4H, t), 3.39 (9H, s), 3.83 (2H, bs), 3.78-3.72 (4H, m), 2.30 (4H, t), 1.88-1.76 (4H, m), 1.70-1.22 (28H, m).

Preparation of Compound d6-3

Compound d6-3 was obtained in a similar manner to that of Compound d4-6, except that the above 1,3-diglyceride was used instead of 1,2-diglyceride.

¹H-NMR (300 MHz, CD₃OD) δ: 7.47 (2H, s), 7.42 (4H, s), 4.62-4.53 (1H, m), 4.38-4.20 (7H, m), 4.10 (4H, t), 2.36 (4H, t), 1.88-1.76 (4H, m), 1.70-1.22 (28H, m).

Preparation of Compound e1-6

6-(Perfluorohexyl)hexanol (6.32 g) was dissolved in dichloromethane (60 mL). The solution was added with triethylamine (3.15 mL), and stirred at 0° C. Further, the solution was added dropwise with methanesulfonyl chloride (1.28 mL), warmed up to room temperature, and stirred. The reaction solution was added with saturated aqueous sodium hydrogen carbonate, and extracted twice with dichloromethane. The resulting organic layer was washed with 1N aqueous hydrochloric acid and saturated brine. After the organic layer was dried over anhydrous magnesium sulfate, the solvent was removed to obtain the corresponding sulfonic ester (7.31 g, 98%).

Sodium hydride (Oil dispersion, 60%) was added with dimethylformamide (DMF) (25 mL), and stirred at 0° C. The solution was added dropwise with a solution of diethyl malonate (2.82 g) dissolved in DMF (3 mL), and warmed up to room temperature. The solution was added dropwise with the above sulfonic ester (7.31 g) dissolved in DMF (10 mL), and stirred at room temperature for two hours, and at 80° C. for two hours. The reaction solution was added with 1N aqueous hydrochloric acid, and extracted twice with dichloromethane. The resulting organic layer was washed with saturated brine. After the organic layer was dried over anhydrous magnesium sulfate, the solvent was removed. The residue was purified by silica gel column chromatography to obtain the corresponding malonate derivative (4.83 g, 58%).

The above malonate derivative (4.83 g) was dissolved in 95% ethanol (70 mL). The solution was added with lithium hydroxide (0.62 g), and stirred at room temperature. The reaction was stopped by addition of 3N hydrochloric acid (1.2 mL). The reaction solution was added with dichloromethane and 1N aqueous hydrochloric acid, and extracted twice with dichloromethane. After the organic layer was dried over anhydrous sodium sulfate, and the solvent was removed. The residue was dissolved in pyridine (20 mL), and the solution was added with concentrated hydrochloric acid (2 mL) and stirred at 130° C. for three hours. The solution was purified by silica gel column chromatography to obtain the corresponding malonic acid derivative (4.83 g, 58%). The reaction solution was added with dichloromethane and 1N aqueous hydrochloric acid, and extracted twice with dichloromethane. The organic layer was dried over anhydrous magnesium sulfate, and the solvent was removed. The residue was purified by silica gel column chromatography to obtain 8-(perfluorohexyl)octanoic acid (3.55 g, 89%).

Sodium hydride (0.8 g) was added with DMF (5 mL) and tetrahydrofuran (THF, 20 mL), and the solution was stirred at 0° C. The solution was added dropwise with a solution of (S)-(+)-2,2-dimethyl-1,3-dioxolan-4-methanol (2.4 g) in mixture of DMF (3 mL) and THF (3 mL), and stirred at 0° C. for one hour. The solution was added with 4-methoxybenzyl chloride (2.8 mL) and stirred at room temperature for three hours. The solution was added with saturated ammonium chloride solution, and extracted twice with ethyl acetate. The resulting organic layer was washed four times with water, once with saturated brine. After the organic layer was dried over anhydrous magnesium sulfate, and the solvent was removed to obtain a crude product of (S)-(+)-4-(4-methoxybenzyloxymethyl)-2,2-dimethyl-1,3-dioxolane (4.1 g, 89%).

The crude product of (S)-(+)-4-(4-methoxybenzyloxymethyl)-2,2-dimethyl-1,3-dioxolane (4.1 g) was dissolved in methanol (10 mL) and the solution was added with 1N hydrochloric acid and stirred at room temperature for one day. The solution was adjusted to pH6 by addition of saturated aqueous sodium hydrogen carbonate, and extracted four times with dichloromethane. After the organic layer was dried over anhydrous sodium sulfate, the solvent was removed. The residue was purified by silica gel column chromatography to obtain (R)-(+)-3-(4-methoxybenzyloxy)-1,2-propandiol (2.4 g, 69%).

(R)-(+)-3-(4-Methoxybenzyloxy)-1,2-propandiol (0.54 g) was dissolved in dichloromethane (3.5 mL) and the solution was added with 8-(perfluorohexyl)octanoic acid (2.32 g), dimethylaminopyridine (28 mg), and ethyl-3-dimethylaminopropyl carbodiimide hydrochloride (EDC-HCl, 1.10 g), and stirred at room temperature for one day. The reaction solution was added with water, extracted twice with dichloromethane. After the resulting organic layer was dried over anhydrous magnesium sulfate, the solvent was removed. The residue was purified by silica gel column chromatography to obtain the 1,2-diglyceride (2.19 g, 78%).

The above 1,2-diglyceride (2.19 g) was added with dichloromethane (40 mL) and water (4 mL), and further with 2,3-dichloro-5,6-dicyano-1,4-benzoquinone (0.69 g). The solution was vigorously stirred at room temperature for two and a half hours. The solution was added with 1N sodium hydroxide, extracted with ethyl acetate, and the resulting organic layer was washed with saturated ammonium chloride and saturated brine. After the organic layer was dried over anhydrous sodium sulfate, and the solvent was removed. The residue was purified by silica gel column chromatography to obtain a deprotected 1,2-diglyceride (1.51 g, 77%).

The above 1,2-diglyceride (0.42 g) was dissolved in dichloromethane (3 mL). To the solution, morpholino acetic acid (75 mg) which was prepared according to the method described in J. Mol. Struct., 560(1-2), 261 (2001), and dimethylaminopyridine (5 mg) were added. Further, the solution was added with ethyl-3-dimethylaminopropyl carbodiimide (0.12 g), and stirred at room temperature for three days. The reaction solution was added with water and extracted twice with dichloromethane. The organic layer was washed with saturated brine. After the resulting organic layer was dried over anhydrous sodium sulfate, the solvent was removed. The residue was purified by silica gel column chromatography to obtain Compound e1-6 (0.40 g, 84%).

$^1$H-NMR (300 MHz, CDCl$_3$) δ: 5.29 (1H, ddt), 4.38 (1H, dd), 4.31 (1H, dd), 4.19 (1H, dd), 4.13 (1H, dd), 3.78-3.72 (4H, m), 3.23 (2H, s), 2.51-2.54 (4H, m), 2.47-2.38 (4H, m), 2.16-1.95 (4H, m), 1.70-1.46 (4H, m), 1.46-1.22 (12H, m).

$^{19}$F-NMR (300 MHz, CDCl$_3$) δ: −81, −114, −122, −123, −124, −126.

Preparation of Compound e2-1

A crude product of morpholino succinic acid can be obtained by reflux of morpholine and succinic acid anhydride dissolved in ethyl acetate, and evaporation of the solvent after the reflux. Compound e2-1 can be obtained in a similar manner to that of Compound e1-6 except that the crude product is used instead of morpholino acetic acid.

Preparation of Compound e2-2

Succinic acid anhydride and the 1,2-diglyceride used for the preparation of Compound e1-6 are dissolved in dichloromethane, and the solution is added with pyridine and dimethylaminopyridine and refluxed. The reaction solution is concentrated and the residue is purified by silica gel column chromatography. Compound e2-2 thus can be obtained.

Preparation of Compound e2-3-3

Compound e2-3-3 can be obtained by a similar condensation reaction using ED-HCL to that of Compound e1-6 by using Compound e2-2 and triethyleneglycol monomethyl ether.

Preparation of Compound e2-5

Compound e2-5 can be obtained in a similar manner to that of Compound e2-3-3 by using Compound e2-2 and 25% aqueous ammonium.

Preparation of Compound e2-6

Compound e2-6 can be obtained according to the method described in J. Med. Chem., 40, 3381 (1997), by using Compound e2-2.

Preparation of Compounds e2-7-2 to e2-7-5

Compounds e2-7-2 to e2-7-5 can be obtained in a similar manner to that of Compound e1-6 except that 3-morpholino propanoic acid, 4-morpholino butanoic acid, 5-morpholino pentanoic acid, or 6-morpholino hexanoic acid which is prepared according to the method described in J. Mol. Struct., 560(1-2), 261 (2001) is used, respectively, instead of morpholino acetic acid.

Preparation of Compound e2-9

Compound e2-9 can be obtained in a similar manner to that of Compound e1-6 except that N,N-dimethylglycine is used instead of morpholino acetic acid.

Preparation of Compound e2-18

2,2-Dimethyl-1,3-dioxolan-4-methanol is dissolved in tetrahydrofuran. The solution is stirred at 0° C. The solution is slowly added with 60% sodium hydride, warmed up to room temperature with stirring, and kept stirred. The solution is again cooled to 0° C., added with chloroacetylmorpholine dissolved in tetrahydrofuran, and stirred at room temperature. The solution is added with water, and extracted with ethyl acetate. The resulting organic layer is washed with saturated brine. After the organic layer is dried over anhydrous magnesium sulfate, removal of the solvent can afford a morpholine-substituted glycerol derivative.

The above glycerol derivative is added with dioxane solution of hydrochloric acid (to 4 mol/L). Removal of the solvent after completion of the reaction can afford the desired diol as a crude product.

Compound e2-18 can be obtained according to the method described in J. Med. Chem., 29(12), 2457 (1986) by using the above diol and 8-(perfluorohexyl) octanoic acid prepared above.

Preparation of Compound e2-16 t-Butyl protected form of Compound e2-16 can be obtained in a similar manner to that of Compound e2-18 except that t-butyl bromoacetate is used instead of chloroacetylmorpholine. The above protected form is dissolved in dichloromethane. The solution is added with trifluoroacetic acid and stirred at room temperature. The reaction solution is added with water and chloroform. After extraction, the obtained organic layer is dried over sodium sulfate. The solvent is removed and the residue is purified by silica gel column chromatography. Compound e2-16 thus can be obtained.

Preparation of Compound e2-10

Cis-1,3-O-benzylidene glycerol is dissolved in tetrahydrofuran, and the solution is stirred at 0° C. The solution is slowly added with 60% sodium hydride, warmed up to room temperature with stirring, and kept stirred. The solution is again cooled to 0° C., added with ethyl bromoacetate dissolved in tetrahydrofuran, and stirred at room temperature. The solution is added with saturated ammonium chloride, and extracted with ethyl acetate. The resulting organic layer is washed with saturated brine and dried over anhydrous magnesium sulfate. Removal of the solvent and the purification of the residue by silica gel column chromatography can afford the glycerol-substituted acetic acid derivative.

The above glycerol-substituted acetic acid derivative is dissolved in ethanol. The solution is added with water and sodium hydroxide and refluxed under heating. The solution is cooled to room temperature, adjusted to pH1 to 2 by using 1N hydrochloric acid, and extracted with chloroform. After the organic layer is dried over anhydrous magnesium sulfate, removal of the solvent can afford the desired carboxylic acid.

Acetal protected form of Compound e2-10 can be obtained in a similar manner to that of Compound e1-6 by using the above carboxylic acid. Further, deprotection reaction using acid similar to that for Compound e2-16 can afford Compound e2-10.

Preparation of Compound e2-11

Compound e2-11 can be obtained in a similar manner to that of Compound e1-6 except that tetrahydro-2-furancarboxylic acid is used instead of morpholino acetic acid.

Preparation of Compound e2-12

Compound e2-12 can be obtained in a similar manner to that of Compound e1-6 except that tetrahydro-3-furancarboxylic acid is used instead of morpholino acetic acid.

Preparation of Compound e2-13

Compound e2-13 can be obtained in a similar manner to that of Compound e1-6 except that 2-furancarboxylic acid is used instead of morpholino acetic acid.

Preparation of Compound e2-17

Compound e2-17 can be obtained in a similar manner to that of Compound e2-5 by using Compound e2-16.

Preparation of Compound e2-20-3

Triethylene glycol monoethyl ether is dissolved in tetrahydrofuran. The solution is added with tosyl chloride, cooled to 0° C., added with triethylamine, and stirred at 0° C. and then at room temperature. The reaction solution is added with 1N hydrochloric acid and ethyl acetate, and extracted with ethyl acetate. After the organic layer is dried over anhydrous sodium sulfate, the solvent is removed. Purification by silica gel column chromatography can afford the desired tosyl form.

Compound e2-20-3 can be obtained in a similar manner to that of Compound e2-18 using the above tosyl form.

Preparation of Compound e2-22

1,2-Glyceride used for the preparation of Compound e1-6 is dissolved in N,N-dimethylformamide, and the solution is stirred at 0° C. After addition of sodium hydride, the solution is warmed up to room temperature, added with 1,3-propane sultone, and further stirred. The reaction solution is added with 1N hydrochloric acid, and extracted with dichloromethane. After the resulting organic layer is dried over anhydrous magnesium sulfate, removal of the solvent can afford Compound e2-22.

Preparation of Compound e3-6

1,3-Dihydroxyacetone (dimer) is dissolved in dichloromethane. The solution is added with 8-(perfluorohexyl) octanoic acid, dimethylaminopyridine, and ethyl-3-dimethylaminopropyl carbodiimide hydrochloride, and stirred at room temperature. After concentration of the reaction solution, purification of the residue by silica gel column chromatography can afford the 1,3-diester.

The above 1,3-diester is dissolved in tetrahydrofuran. The solution is added with water and stirred at 0° C. The solution is slowly added with sodium borohydride, and kept stirred still at 0° C. After addition of saturated ammonium chloride, the solution is extracted with dichloromethane. The resulting organic layer is washed with saturated brine, and dried over sodium sulfate. Evaporation of the solvent and purification of the residue by silica gel column chromatography can afford the 1,3-diglyceride.

Compound e3-6 can be obtained in a similar manner to that of Compound e1-6 by using the above 1,3-diglyceride.

Preparation of Compound e4-1

Compound e4-1 can be obtained in a similar manner to that of Compound e2-1 except that the above 1,3-diglyceride is used instead of 1,2-diglyceride.

Preparation of Compound e4-2

Compound e4-2 can be obtained in a similar manner to that of Compound e2-2 except that the above 1,3-diglyceride is used instead of 1,2-diglyceride.

Preparation of Compound e4-3-3

Compound e4-3-3 can be obtained in a similar manner to that of Compound e2-3-3 except that the above 1,3-diglyceride is used instead of 1,2-diglyceride.

Preparation of Compound e4-5

Compound e4-5 can be obtained in a similar manner to that of Compound e2-5 except that the above 1,3-diglyceride is used instead of 1,2-diglyceride.

Preparation of Compound e4-6

Compound e4-6 can be obtained in a similar manner to that of Compound e2-6 except that the above 1,3-diglyceride is used instead of 1,2-diglyceride.

Preparation of Compound e4-7-2 to e4-7-5

Compounds e4-7-2 to e4-7-5 can be obtained in a similar manner to those of Compounds e2-7-2 to e2-7-5, respectively, except that the above 1,3-diglyceride is used instead of 1,2-diglyceride.

Preparation of Compound e4-9

Compound e4-9 can be obtained in a similar manner to that of Compound e2-9 except that the above 1,3-diglyceride is used instead of 1,2-diglyceride.

Preparation of Compound e4-10

Compound e4-10 can be obtained in a similar manner to that of Compound e2-10 except that the above 1,3-diglyceride is used instead of 1,2-diglyceride.

Preparation of Compound e4-11

Compound e4-11 can be obtained in a similar manner to that of Compound e2-11 except that the above 1,3-diglyceride is used instead of 1,2-diglyceride.

Preparation of Compound e4-12

Compound e4-12 can be obtained in a similar manner to that of Compound e2-12 except that the above 1,3-diglyceride is used instead of 1,2-diglyceride.

Preparation of Compound e4-13

Compound e4-13 can be obtained in a similar manner to that of Compound e2-13 except that the above 1,3-diglyceride is used instead of 1,2-diglyceride.

Preparation of Compound e4-16

Compound e4-16 can be obtained in a similar manner to that of Compound e2-16 except that the above 1,3-diglyceride is used instead of 1,2-diglyceride.

Preparation of Compound e4-17

Compound e4-17 can be obtained in a similar manner to that of Compound e2-17 except that the above 1,3-diglyceride is used instead of 1,2-diglyceride.

Preparation of Compound e4-18

Compound e4-18 can be obtained in a similar manner to that of Compound e2-18 except that the above 1,3-diglyceride is used instead of 1,2-diglyceride.

Preparation of Compound e4-20-3

Compound e4-20-3 can be obtained in a similar manner to that of Compound e2-20-3 except that the above 1,3-diglyceride is used instead of 1,2-diglyceride.

Preparation of Compound e4-22

Compound e4-22 can be obtained in a similar manner to that of Compound e2-22 except that the above 1,3-diglyceride is used instead of 1,2-diglyceride.

Preparation of Compound e4-21-1

2-(Cis-1,3-O-benzylidene glyceroyl)ethanol can be obtained by the method described in Arch. Pharm. (Weinheim), 328, 271 (1995). The compound is protected with t-butyldimethylsilyl (TBS) protective group according to the method described in "Protecting groups in organic synthesis" (John Wiley & sons, inc.) written by T. W. Green & P. G. M. Wuts, and TBS protected form of Compound e4-21-1 thus can be obtained in a similar manner to that of Compound e2-18. Compound e4-21-1 can be obtained by removal of TBS group by deprotection according to the method described in "Protecting groups in organic synthesis" as described above.

Test Example 1

Preparation Method of Liposome

According to the method described in J. Med. Chem., 25 (12), 1500 (1982), the disclosure of which is expressly incorporated by reference herein in its entirety, dipalmitoyl-PC (Funakoshi, No. 1201-41-0225), dipalmitoyl-PS (Funakoshi, No. 1201-42-0237), and the compound of the present invention, in the ratio described below, were dissolved in chloroform contained in an eggplant-shaped flask to obtain a uniform solution, and then the solvent was evaporated under reduced pressure to obtain a thin membrane formed on the bottom of the flask. The thin membrane was dried in vacuo, then added with an appropriate volume of 0.9% physiological saline (Hikari Pharmaceutical, No. 512) and ultrasonicated (probe type oscillator, Branson, No. 3542, 0.1 mW) for 5 minute with ice cooling to obtain a uniform liposome dispersion. Size of the particles contained in the resulting dispersion was measured by using WBC analyzer (Nihon Kohden, A-1042). The particle sizes were 85 to 110 nm. As shown below, it is clear that the compound of the present invention can be efficiently encapsulated in the liposome of the following composition, and thus the compound has superior features as a component lipid of liposomes for a contrast medium.

|  | Maximum amount forming liposome |
|---|---|
| PC 50 nmol + PS 50 nmol + a2-6 | 5 nmol |
| PC 50 nmol + PS 50 nmol + b1-1 | 40 nmol |
| PC 50 nmol + PS 50 nmol + b1-2 | 40 nmol |
| PC 50 nmol + PS 50 nmol + b1-8 | 20 nmol |
| PC 50 nmol + PS 50 nmol + b4-2 | 20 nmol |
| PC 50 nmol + PS 50 nmol + c1-5 | 20 nmol |
| PC 50 nmol + PS 50 nmol + d1-6 | 40 nmol |
| PC 50 nmol + PS 50 nmol + d3-6 | 40 nmol |
| PC 50 nmol + PS 50 nmol + d4-6 | 20 nmol |
| PC 50 nmol + PS 50 nmol + d5-6 | 20 nmol |
| PC 50 nmol + PS 50 nmol + d6-2 | 20 nmol |
| PC 50 nmol + PS 50 nmol + d6-3 | 20 nmol |
| PC 50 nmol + PS 50 nmol + e1-6 | 40 nmol |

Test Example 2

Introduced Amount of the Compounds to Vascular Smooth Muscle Cells

The above liposome agent was added to a mixture culture system of vascular smooth muscle cells and macrophage, described in WO 01/082897, the disclosure of which is expressly incorporated by reference herein in its entirety. After cultivation under 37° C., 5% $CO_2$ for 24 hours, the amount of the compounds introduced to the vascular smooth muscle cells were quantitated. As shown below, it is clear that the compound of the present invention can be efficiently introduced to vascular smooth muscle cells, and thus the compound has superior features as a component lipid of liposomes for a contrast medium.

|  | Introduced amount |
|---|---|
| PC 50 nmol + PS 50 nmol + b1-1 | 17.5 nmol/mg protein |
| PC 50 nmol + PS 50 nmol + b1-2 | 16.4 nmol/mg protein |
| PC 50 nmol + PS 50 nmol + b1-8 | 8.9 nmol/mg protein |
| PC 50 nmol + PS 50 nmol + b4-2 | 10.6 nmol/mg protein |
| PC 50 nmol + PS 50 nmol + d1-6 | 17.1 nmol/mg protein |
| PC 50 nmol + PS 50 nmol + d3-6 | 16.8 nmol/mg protein |
| PC 50 nmol + PS 50 nmol + d4-6 | 12.1 nmol/mg protein |
| PC 50 nmol + PS 50 nmol + d5-6 | 11.8 nmol/mg protein |
| PC 50 nmol + PS 50 nmol + d6-2 | 11.5 nmol/mg protein |
| PC 50 nmol + PS 50 nmol + d6-3 | 12.8 nmol/mg protein |

Test Example 3

Toxicity Test by Continuous Administration for 3 Days in Mice

Six-week old ICR male mice (Charles River Japan) were purchased, and after quarantine for 1 week, acclimatized for 1 week in a clean animal cage (air-conditioning: HEPA filter of class 1000, room temperature: 20 to 24° C., humidity: 35 to 60%). Then, in order to obtain the MTD value, a suspension of the test compound was administered from the caudal vein. The suspension was administered by using physiological saline (Hikari Pharmaceutical) or a glucose solution (Otsuka Pharmaceutical) as a medium. On the basis of the MTD value obtained, the suspension was administered everyday from the caudal vein for three consecutive days in an amount corresponding to ½ of the MTD value (n=3). Symptoms were observed up to 6 hours after each administration to observe neurotoxicity, and then autopsy was performed to examine major organs. It is clearly understood that the compound of the present invention has low toxicity and no neurotoxicity, and thus the compound has superior features as a component lipid of liposomes for a contrast medium.

Compound (MTD (mg/kg)): neurotoxicity ("−" indicates negative for neurotoxicity, and "+" indicate positive for neurotoxicity)

Compound a2-6: 800 mg/kg:—

Compound b1-1: 400 mg/kg:—

Compound b1-2: 400 mg/kg:—

Compound b1-8: 400 mg/kg:—

Compound b4-2: 400 mg/kg:—

Compound c1-5: 400 mg/kg:—

Compound d1-6: 400 mg/kg:—

Compound d3-6: 400 mg/kg:—

Compound d4-6: 400 mg/kg:—

Compound d5-6: 400 mg/kg:—

Compound d6-2: 400 mg/kg:—

Compound d6-3: 400 mg/kg:—

Compound e1-6: 400 mg/kg:—

Test Example 4

MRI Test of Watanabe Rabbit

Watanabe Heritable Hyperlipidemic Rabbit: WHHL

Liposome formulation having the ratio of PC:PS:Compound d1-6=50:50:40 (nmol), and a particle sizes of 85 to 120 nm are prepared from a chloroform solution of PC (dipalmitoyl-phosphatidylcholine Funakoshi, No. 850355C), PS (di-palmitoyl-phosphatidylserine Funakoshi, No. 840037C), and Compound d1-6.

Injection solvent (manufactured by Otsuka Pharmaceutical Co., Ltd.) was used for the formulation.

Figure 2:
FIG. 2 is a photograph presenting the result of MRI imaging ($^{19}F$-MRI) of arteriosclerotic lesion in aortic arch of WHHL rabbit by using a liposome of the present invention.
Figure 3:
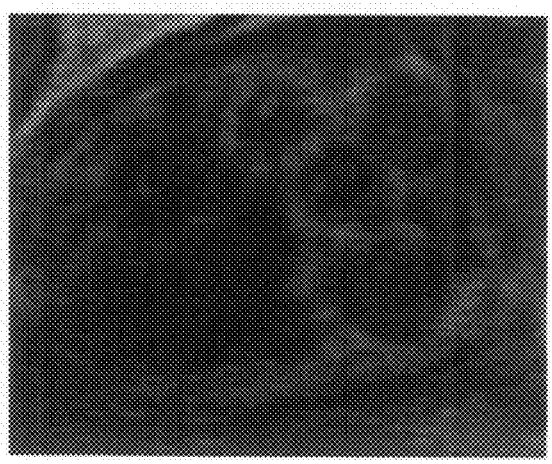
FIG. 3 is a photograph presenting superposition of MRI images shown in FIGS. 1 and 2.

Twelve-month old WHHL rabbit (Kitayama Labes) having lesion formed in aotic arch were obtained, and kept for acclimatization for 1 week. The above liposome formulation was administered from subaural vein (80 mg/kg as Compound d1-6). After 15 minutes, fluorine MRI targeting the lesion in arch was conducted. The results are shown in FIGS. 1 to 3. The figures show accumulation of the contrast medium in aotic arch, and contrast imaging of the lesion was succeeded Results similar to the above can be obtained by using another compound of the present invention instead of Compound d1-6.

INDUSTRIAL APPLICABILITY

The compounds or the salts thereof according to the present invention have superior feature in the amount introduced to liposome as a component lipid of a liposome for a contrast medium. Contrast imaging of a lesion of a vessel can be selectively conducted by using the liposomes comprising said compounds or the salts thereof.

The invention claimed is:

1. A compound represented by the following general formula (Id) or (IId), or a salt thereof:

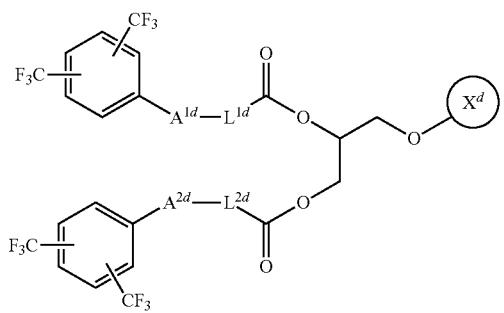

(Id)

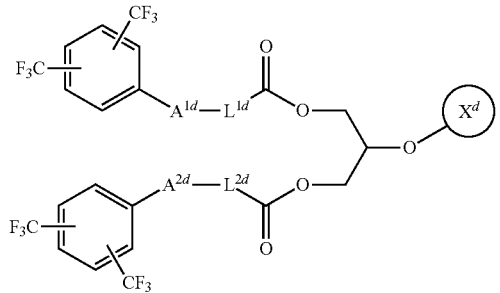

(IId)

wherein $A^{1d}$ and $A^{2d}$ each independently represents an oxygen atom or a single bond; $L^{1d}$ and $L^{2d}$ each independently represents a divalent bridging group comprising a main chain consisting of 5 to 20 carbon atoms; and $X^d$ is selected from the group consisting of:

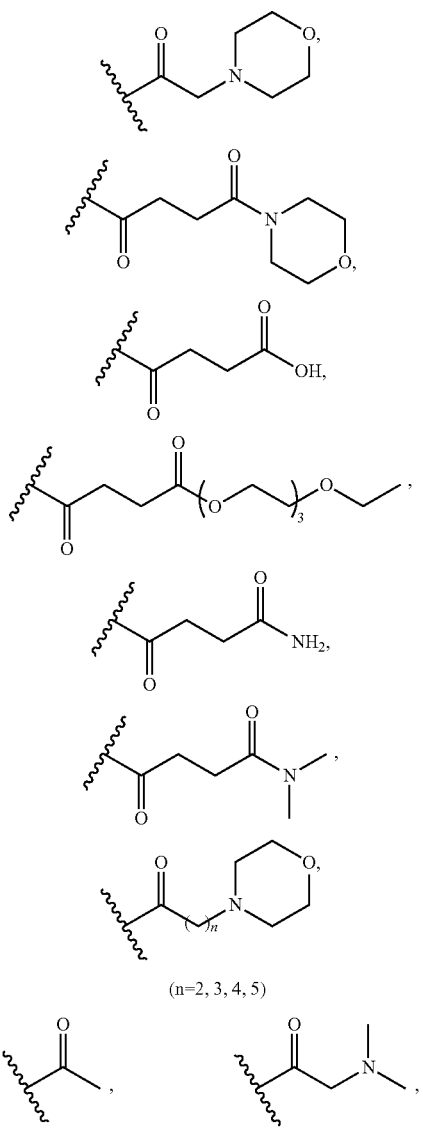

(n=2, 3, 4, 5)

-continued

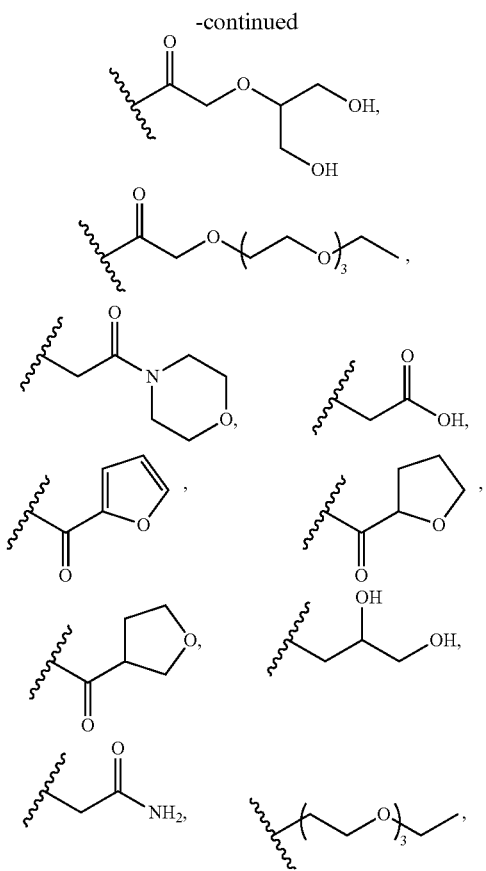

-continued

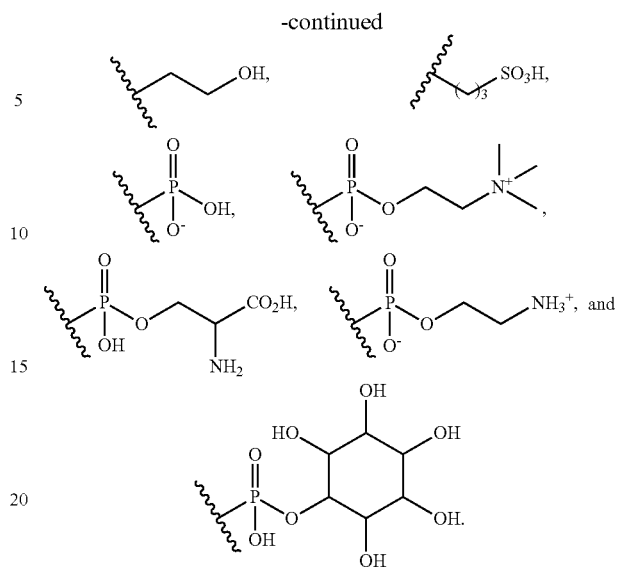

2. A liposome containing as a membrane component the compound or a salt thereof according to claim 1.

3. The liposome according to claim 2, which contains a phosphatidylcholine and a phosphatidylserine as membrane components.

4. A method of contrast imaging, which comprises administering the liposome according to claim 2 to a mammal including human.

5. The method of claim 4, wherein the mammal is a human.

* * * * *